US009554982B2

(12) United States Patent
Swaile et al.

(10) Patent No.: US 9,554,982 B2
(45) Date of Patent: *Jan. 31, 2017

(54) AEROSOL ANTIPERSPIRANT COMPOSITIONS, PRODUCTS AND METHODS

(71) Applicant: The Procter & Gamble Company, Cincinnati, OH (US)

(72) Inventors: David Frederick Swaile, Cincinnati, OH (US); Rajeev Kumar Passi, West Chester, OH (US); Ann Christine Zoller, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/026,614

(22) Filed: Sep. 13, 2013

(65) Prior Publication Data

US 2014/0077003 A1 Mar. 20, 2014

Related U.S. Application Data

(60) Provisional application No. 61/701,201, filed on Sep. 14, 2012.

(51) Int. Cl.
| | |
|---|---|
| *A61K 8/891* | (2006.01) |
| *A61Q 15/00* | (2006.01) |
| *A61K 8/04* | (2006.01) |
| *B65D 83/44* | (2006.01) |
| *B65D 83/14* | (2006.01) |
| *A61K 8/02* | (2006.01) |
| *B65D 83/46* | (2006.01) |

(52) U.S. Cl.
CPC ............ *A61K 8/891* (2013.01); *A61K 8/0241* (2013.01); *A61K 8/046* (2013.01); *A61Q 15/00* (2013.01); *B65D 83/44* (2013.01); *B65D 83/46* (2013.01); *B65D 83/752* (2013.01); *A61K 2800/87* (2013.01)

(58) Field of Classification Search
CPC ...... A61K 8/891; A61K 8/046; A61K 8/0241; A61K 2800/87; A61Q 15/00; B65D 83/44; B65D 83/752; B65D 83/46
See application file for complete search history.

(56) References Cited

U.S. PATENT DOCUMENTS

| | | | |
|---|---|---|---|
| 2,890,817 A | 6/1959 | Rheinstrom | |
| 4,383,988 A | 5/1983 | Teng et al. | |
| 4,396,152 A | 8/1983 | Abplanalp | |
| 4,605,553 A | 8/1986 | Passalacqua | |
| 4,724,139 A | 2/1988 | Palinczar | |
| 4,806,338 A | 2/1989 | Smith | |
| 4,822,603 A | 4/1989 | Farris et al. | |
| 4,840,789 A | 6/1989 | Orr et al. | |
| 4,853,214 A | 8/1989 | Orr | |
| 4,863,721 A | 9/1989 | Beck et al. | |
| 4,889,711 A | 12/1989 | Kai et al. | |
| 4,985,238 A | 1/1991 | Tanner et al. | |
| 5,019,375 A | 5/1991 | Tanner et al. | |
| 5,069,897 A | 12/1991 | Orr | |
| 5,082,652 A | 1/1992 | Mayfield et al. | |
| 5,169,626 A | 12/1992 | Tanner et al. | |
| 5,176,903 A | 1/1993 | Goldberg et al. | |
| 5,178,881 A | 1/1993 | Mackles et al. | |
| 5,294,447 A | 3/1994 | Mackles et al. | |
| 5,298,236 A | 3/1994 | Orr et al. | |
| 5,378,452 A | 1/1995 | Greczyn | |
| 5,400,920 A | 3/1995 | Barnhart | |
| 5,417,357 A | 5/1995 | Yquel | |
| 5,417,964 A | 5/1995 | Carlson, Sr. et al. | |
| 5,444,096 A | 8/1995 | McCrea et al. | |
| 5,449,511 A | 9/1995 | Coe | |
| 5,593,069 A | 1/1997 | Jinks | |
| 5,605,682 A | 2/1997 | Ross et al. | |

(Continued)

FOREIGN PATENT DOCUMENTS

| | | |
|---|---|---|
| AU | 2007100166 A4 | 3/2007 |
| DE | 4439443 | 5/1996 |

(Continued)

OTHER PUBLICATIONS

PCT International Search Report and Written Opinion for PCT/US2013/068982, dated Mar. 14, 2014.
International Search Report and Written Opinion of the International Searching Authority, Application No. PCT/US2013/059685, mailed Nov. 17, 2014, 12 pages.
All Office Actions, U.S. Appl. No. 14/026,434.
All Office Actions, U.S. Appl. No. 14/307,433.
All Office Actions, U.S. Appl. No. 14/307,457.
All Office Actions, U.S. Appl. No. 14/307,462.
All Office Actions, U.S. Appl. No. 14/307,466.
All Office Actions, U.S. Appl. No. 14/307,438.
All Office Actions, U.S. Appl. No. 14/307,447.
All Office Actions, U.S. Appl. No. 14/307,455.
All Office Actions, U.S. Appl. No. 14/656,118.
All Office Actions, U.S. Appl. No. 14/656,144.

(Continued)

*Primary Examiner* — Sean Basquill

(57) ABSTRACT

An aerosol antiperspirant composition is provided. The aerosol antiperspirant composition includes a propellant and an antiperspirant composition. The antiperspirant composition includes one or more liquid materials, wherein the one or more liquid materials comprise one or more non-volatile silicone fluids having a concentration from 40% to about 70% by weight of the antiperspirant composition; antiperspirant active particulates having a concentration from about 16% to about 32% by weight of the antiperspirant composition; one or more non-antiperspirant active particulates that are substantially inert, wherein the one or more non-antiperspirant active particulates that are substantially inert have a concentration from 10% to 30% by weight of the antiperspirant composition; and wherein the antiperspirant composition has a total particulate concentration from 30% to about 60% by weight of the antiperspirant composition.

17 Claims, 11 Drawing Sheets

(56) References Cited

U.S. PATENT DOCUMENTS

| | | |
|---|---|---|
| 5,609,300 A | 3/1997 | Conatser |
| 5,623,920 A | 4/1997 | Bryant |
| 5,628,989 A | 5/1997 | Harashima et al. |
| 5,628,990 A | 5/1997 | Murphy et al. |
| 5,639,219 A | 6/1997 | Conatser |
| 5,657,790 A | 8/1997 | Mohn |
| 5,690,256 A | 11/1997 | Smith |
| 5,697,532 A | 12/1997 | Wilde et al. |
| 5,718,890 A | 2/1998 | Putnam et al. |
| 5,735,465 A | 4/1998 | Laforcade |
| 5,750,096 A | 5/1998 | Guskey |
| 5,756,082 A | 5/1998 | Cashin et al. |
| 5,770,187 A | 6/1998 | Hasebe et al. |
| 5,772,085 A | 6/1998 | Bryant et al. |
| 5,785,301 A | 7/1998 | Scheindel |
| 5,794,660 A | 8/1998 | Mohn |
| 5,803,319 A | 9/1998 | Smith et al. |
| 5,833,964 A | 11/1998 | Linn et al. |
| 5,840,286 A | 11/1998 | Gardlik et al. |
| 5,840,287 A | 11/1998 | Guskey et al. |
| 5,840,288 A | 11/1998 | Guskey et al. |
| 5,840,289 A | 11/1998 | Hall |
| 5,843,414 A | 12/1998 | Hilvert et al. |
| 5,846,520 A | 12/1998 | Guskey et al. |
| 5,849,276 A | 12/1998 | Guskey et al. |
| 5,871,717 A | 2/1999 | Bretzler et al. |
| 5,891,424 A | 4/1999 | Bretzler et al. |
| 5,891,425 A | 4/1999 | Bretzler et al. |
| 5,895,644 A | 4/1999 | Albanese et al. |
| 5,902,570 A | 5/1999 | Bretzler et al. |
| 5,906,046 A | 5/1999 | Abplanalp et al. |
| 5,921,439 A | 7/1999 | Losenno et al. |
| 5,927,563 A | 7/1999 | Kellner |
| 5,932,199 A | 8/1999 | Esser |
| 5,939,056 A | 8/1999 | Fletcher et al. |
| 5,941,424 A | 8/1999 | Hildebrandt |
| 5,945,085 A | 8/1999 | Salas et al. |
| 5,957,333 A | 9/1999 | Losenno et al. |
| 5,957,342 A | 9/1999 | Gallien |
| 5,967,382 A | 10/1999 | Lasserre et al. |
| 5,972,319 A | 10/1999 | Linn et al. |
| 5,985,252 A | 11/1999 | Hall et al. |
| 6,006,954 A | 12/1999 | Warby |
| 6,039,306 A | 3/2000 | Pericard et al. |
| 6,045,784 A | 4/2000 | Ruebusch et al. |
| 6,048,518 A | 4/2000 | Bianchi et al. |
| 6,070,770 A | 6/2000 | Tada et al. |
| 6,083,492 A | 7/2000 | Modi |
| 6,092,698 A | 7/2000 | Bayer |
| 6,110,449 A | 8/2000 | Bacon et al. |
| 6,112,945 A | 9/2000 | Woods |
| 6,112,950 A | 9/2000 | Di Giovanni et al. |
| 6,113,070 A | 9/2000 | Holzboog |
| 6,123,932 A | 9/2000 | Guskey et al. |
| 6,132,744 A | 10/2000 | Chehab et al. |
| 6,136,302 A | 10/2000 | Juneja et al. |
| 6,136,303 A | 10/2000 | Ruebusch et al. |
| 6,145,712 A | 11/2000 | Benoist |
| 6,171,601 B1 | 1/2001 | Gardlik et al. |
| 6,187,300 B1 | 2/2001 | Motley et al. |
| 6,187,301 B1 | 2/2001 | Scavone et al. |
| 6,197,286 B1 | 3/2001 | Scavone et al. |
| 6,231,841 B1 | 5/2001 | Franklin et al. |
| 6,245,324 B1 | 6/2001 | Hough et al. |
| 6,261,543 B1 | 7/2001 | Fletcher et al. |
| 6,296,155 B1 | 10/2001 | Smith |
| 6,299,024 B1 | 10/2001 | Corba |
| 6,318,603 B1 | 11/2001 | Burt |
| 6,342,210 B1 | 1/2002 | Cai et al. |
| 6,352,688 B1 | 3/2002 | Scavone et al. |
| 6,357,633 B1 | 3/2002 | Zimmerhackel et al. |
| 6,361,765 B1 | 3/2002 | Emslie et al. |
| 6,361,766 B1 | 3/2002 | Franklin et al. |
| 6,375,036 B1 | 4/2002 | Woods |
| 6,375,378 B1 | 4/2002 | Kitaura |
| 6,375,938 B1 | 4/2002 | Clothier, Jr. et al. |
| 6,382,474 B1 | 5/2002 | Woods et al. |
| 6,383,476 B1 | 5/2002 | Scavone et al. |
| 6,387,356 B1 | 5/2002 | Csernica et al. |
| 6,387,358 B2 | 5/2002 | Chuah et al. |
| 6,394,364 B1 | 5/2002 | Abplanalp |
| 6,403,067 B1 | 6/2002 | Schamper et al. |
| 6,403,072 B1 | 6/2002 | Scavone et al. |
| 6,416,750 B1 | 7/2002 | Harper et al. |
| 6,418,920 B1 | 7/2002 | Marr |
| 6,425,503 B1 | 7/2002 | Scheindel |
| 6,426,062 B1 | 7/2002 | Chopra et al. |
| 6,428,777 B1 | 8/2002 | Boyle et al. |
| 6,431,413 B2 | 8/2002 | Corba |
| 6,436,382 B1 | 8/2002 | Chopra et al. |
| 6,454,140 B1 | 9/2002 | Jinks |
| 6,468,511 B1 | 10/2002 | Chopra et al. |
| 6,488,919 B1 | 12/2002 | Murphy et al. |
| 6,510,969 B2 | 1/2003 | Di Giovanni et al. |
| 6,534,046 B1 | 3/2003 | Golz-Berner et al. |
| 6,555,098 B1 | 4/2003 | Murphy et al. |
| 6,588,627 B2 | 7/2003 | Petterson et al. |
| 6,588,628 B2 | 7/2003 | Abplanalp et al. |
| 6,588,631 B2 | 7/2003 | Sanchez |
| RE38,207 E | 8/2003 | Benoist |
| 6,607,106 B2 | 8/2003 | Henry et al. |
| 6,610,279 B2 | 8/2003 | Chopra et al. |
| 6,619,515 B1 | 9/2003 | Abplanalp et al. |
| 6,640,805 B2 | 11/2003 | Castro et al. |
| 6,644,306 B1 | 11/2003 | Riebe et al. |
| 6,645,475 B2 | 11/2003 | Franklin et al. |
| 6,652,843 B2 | 11/2003 | Fairclough et al. |
| 6,703,005 B2 | 3/2004 | Allan et al. |
| 6,719,965 B2 | 4/2004 | Tomczak |
| 6,726,901 B2 | 4/2004 | Yin et al. |
| 6,749,841 B2 | 6/2004 | Joshi et al. |
| 6,793,915 B1 | 9/2004 | Guenin et al. |
| 6,805,855 B2 | 10/2004 | Mattai et al. |
| 6,849,251 B2 | 2/2005 | Banowski et al. |
| 6,978,196 B2 | 12/2005 | Albertus |
| 6,978,915 B1 | 12/2005 | Russell |
| 6,978,916 B2 | 12/2005 | Smith |
| 6,986,885 B2 | 1/2006 | Mattai et al. |
| 6,994,845 B2 | 2/2006 | Mattai et al. |
| 7,033,579 B1 | 4/2006 | Scavone |
| 7,086,571 B2 | 8/2006 | Warby et al. |
| 7,128,901 B2 | 10/2006 | Jonas et al. |
| 7,235,261 B2 | 6/2007 | Smith et al. |
| 7,261,225 B2 | 8/2007 | Rueschhoff et al. |
| 7,278,556 B2 | 10/2007 | Goujon et al. |
| 7,329,403 B2 | 2/2008 | Chuah et al. |
| 7,341,169 B2 | 3/2008 | Bayer |
| 7,341,984 B2 | 3/2008 | Wilson et al. |
| 7,364,055 B2 | 4/2008 | Yquel et al. |
| 7,404,946 B2 | 7/2008 | Bowens-Jones et al. |
| 7,465,698 B2 | 12/2008 | Wilson et al. |
| 7,479,477 B2 | 1/2009 | Wilson et al. |
| 7,501,136 B2 | 3/2009 | Hagura et al. |
| 7,563,384 B2 | 7/2009 | Thomas et al. |
| 7,597,818 B2 | 10/2009 | Singh et al. |
| 7,605,117 B2 | 10/2009 | Wilson et al. |
| 7,622,435 B2 | 11/2009 | Wilson et al. |
| 7,735,696 B2 | 6/2010 | Allsop |
| 7,744,857 B2 | 6/2010 | Beachy et al. |
| 7,766,030 B2 | 8/2010 | Askew |
| 7,790,202 B1 | 9/2010 | Martell |
| 7,793,805 B2 | 9/2010 | Allsop |
| 7,793,806 B2 | 9/2010 | Allsop |
| 7,799,318 B2 | 9/2010 | Esposito et al. |
| 7,833,433 B2 | 11/2010 | Singh et al. |
| 7,959,041 B2 | 6/2011 | Miller et al. |
| 7,997,458 B2 | 8/2011 | Wickham |
| 7,997,459 B2 | 8/2011 | Warby |
| 8,002,247 B2 | 8/2011 | Birtcher et al. |
| 8,008,244 B2 | 8/2011 | Knopeck et al. |
| 8,075,796 B2 | 12/2011 | Rao et al. |
| 8,097,181 B2 | 1/2012 | Leck et al. |
| 8,101,094 B2 | 1/2012 | Howell et al. |
| 8,114,828 B2 | 2/2012 | Bowman et al. |

(56) References Cited

U.S. PATENT DOCUMENTS

| | | |
|---|---|---|
| 8,133,407 B2 | 3/2012 | Zyhowski et al. |
| 8,147,709 B2 | 4/2012 | Mahler et al. |
| 8,148,317 B2 | 4/2012 | Singh et al. |
| 8,210,400 B2 | 7/2012 | Scheindel |
| 8,257,689 B2 | 9/2012 | Pan |
| 8,333,902 B2 | 12/2012 | Mahler et al. |
| 8,349,339 B2 | 1/2013 | Cropper et al. |
| 8,388,857 B2 | 3/2013 | Elsheikh et al. |
| 8,393,554 B2 | 3/2013 | Yamamoto et al. |
| 8,394,286 B2 | 3/2013 | Leck et al. |
| 8,399,713 B2 | 3/2013 | Bartelt et al. |
| 8,444,874 B2 | 5/2013 | Singh et al. |
| 8,496,846 B2 | 7/2013 | Rao et al. |
| 8,518,384 B2 | 8/2013 | Fletcher et al. |
| 8,529,786 B2 | 9/2013 | Leck et al. |
| 8,535,555 B2 | 9/2013 | Feiring et al. |
| 8,557,260 B2 | 10/2013 | Falk |
| 8,590,755 B2 | 11/2013 | Davideit et al. |
| 8,596,557 B2 | 12/2013 | Yamamoto et al. |
| 8,597,622 B2 | 12/2013 | Lemoine et al. |
| 8,628,681 B2 | 1/2014 | Low |
| 8,637,443 B2 | 1/2014 | Basu et al. |
| 8,663,494 B2 | 3/2014 | Howell et al. |
| 2002/0034481 A1 | 3/2002 | Bianchi et al. |
| 2002/0039563 A1 | 4/2002 | Franklin et al. |
| 2002/0079337 A1 | 6/2002 | Jinks |
| 2002/0164296 A1 | 11/2002 | Schamper et al. |
| 2002/0190085 A1 | 12/2002 | Stanford |
| 2003/0010794 A1 | 1/2003 | Herdtle et al. |
| 2003/0024953 A1 | 2/2003 | Peter Lilienthal |
| 2003/0053970 A1 | 3/2003 | Bruening et al. |
| 2003/0071080 A1 | 4/2003 | Yquel |
| 2003/0113282 A1 | 6/2003 | Buranachokpaisan |
| 2003/0161800 A1 | 8/2003 | Guenin et al. |
| 2003/0235545 A1 | 12/2003 | Guenin et al. |
| 2003/0235546 A1 | 12/2003 | Mattai et al. |
| 2004/0141934 A1 | 7/2004 | Fei et al. |
| 2004/0202630 A1 | 10/2004 | Joshi et al. |
| 2004/0213748 A1 | 10/2004 | Chuah et al. |
| 2004/0222244 A1 | 11/2004 | Groeger |
| 2004/0241123 A1 | 12/2004 | Popoff et al. |
| 2004/0265254 A1 | 12/2004 | Tomczak |
| 2005/0084510 A1 | 4/2005 | Carson |
| 2005/0169851 A1 | 8/2005 | Smith |
| 2005/0191257 A1 | 9/2005 | Brahms et al. |
| 2005/0281767 A1 | 12/2005 | Walling et al. |
| 2006/0029624 A1 | 2/2006 | Banowski et al. |
| 2006/0033072 A1 | 2/2006 | Wilson et al. |
| 2006/0039877 A1 | 2/2006 | Mattai et al. |
| 2006/0104918 A1* | 5/2006 | Brown et al. ............. 424/47 |
| 2006/0210502 A1 | 9/2006 | Galante et al. |
| 2006/0263311 A1 | 11/2006 | Scavone et al. |
| 2006/0263312 A1 | 11/2006 | Scavone et al. |
| 2006/0269484 A1 | 11/2006 | Knopeck et al. |
| 2007/0003499 A1 | 1/2007 | Shen et al. |
| 2007/0036738 A1* | 2/2007 | Fletcher et al. ............. 424/65 |
| 2007/0092463 A1 | 4/2007 | Kim et al. |
| 2007/0098646 A1 | 5/2007 | Nappa et al. |
| 2007/0248551 A1 | 10/2007 | Lemoine et al. |
| 2007/0292460 A1 | 12/2007 | Schiemann et al. |
| 2008/0098600 A1 | 5/2008 | Riebe et al. |
| 2008/0121666 A1 | 5/2008 | Purkins |
| 2008/0157022 A1 | 7/2008 | Singh et al. |
| 2008/0166305 A1 | 7/2008 | Singh et al. |
| 2008/0171652 A1 | 7/2008 | Singh et al. |
| 2008/0187504 A1 | 8/2008 | Fan et al. |
| 2008/0187562 A1 | 8/2008 | Fan et al. |
| 2008/0190418 A1 | 8/2008 | Miller et al. |
| 2008/0213322 A1 | 9/2008 | Birman et al. |
| 2008/0224082 A1 | 9/2008 | Warby |
| 2008/0230566 A1 | 9/2008 | Frutin |
| 2008/0233067 A1 | 9/2008 | Lee et al. |
| 2008/0292564 A1 | 11/2008 | Singh et al. |
| 2008/0317694 A1 | 12/2008 | Bruening et al. |
| 2009/0047226 A1 | 2/2009 | Teckenbrock et al. |
| 2009/0078902 A1 | 3/2009 | Flynn |
| 2009/0087396 A1 | 4/2009 | Hwang et al. |
| 2009/0117066 A1 | 5/2009 | Massaro et al. |
| 2009/0145932 A1 | 6/2009 | Davideit et al. |
| 2009/0220555 A1 | 9/2009 | Hwang et al. |
| 2009/0253612 A1* | 10/2009 | Mushock et al. ............. 512/4 |
| 2009/0304617 A1 | 12/2009 | Banowski et al. |
| 2009/0317345 A1 | 12/2009 | Joshi et al. |
| 2010/0044400 A1 | 2/2010 | Laidler |
| 2010/0051651 A1 | 3/2010 | Allsop |
| 2010/0104612 A1 | 4/2010 | Cropper et al. |
| 2010/0104613 A1 | 4/2010 | Chan et al. |
| 2010/0112022 A1 | 5/2010 | Hoying et al. |
| 2010/0122545 A1 | 5/2010 | Minor et al. |
| 2010/0200799 A1 | 8/2010 | Mouli |
| 2010/0224656 A1 | 9/2010 | Scheindel |
| 2010/0260698 A1 | 10/2010 | Galante et al. |
| 2011/0005723 A1 | 1/2011 | Mouli |
| 2011/0031436 A1 | 2/2011 | Mahler et al. |
| 2011/0232939 A1 | 9/2011 | Luly et al. |
| 2011/0253927 A1 | 10/2011 | Minor et al. |
| 2011/0257282 A1 | 10/2011 | Alexander |
| 2011/0275723 A1 | 11/2011 | Hulse et al. |
| 2012/0003284 A1 | 1/2012 | Arnaud et al. |
| 2012/0074349 A1 | 3/2012 | Leck et al. |
| 2012/0076839 A1 | 3/2012 | Chan et al. |
| 2012/0107261 A1 | 5/2012 | Banowski et al. |
| 2012/0126187 A1 | 5/2012 | Low |
| 2012/0138639 A1 | 6/2012 | Scheindel |
| 2012/0141385 A1 | 6/2012 | Bowman et al. |
| 2012/0168663 A1 | 7/2012 | Singh et al. |
| 2012/0177589 A1 | 7/2012 | Banowski et al. |
| 2012/0187330 A1 | 7/2012 | Singh et al. |
| 2012/0305480 A1 | 12/2012 | Low |
| 2012/0305830 A1 | 12/2012 | Low |
| 2012/0318828 A1 | 12/2012 | Nappa et al. |
| 2013/0032751 A1 | 2/2013 | Low |
| 2013/0161554 A1 | 6/2013 | Elsheikh et al. |
| 2013/0187078 A1 | 7/2013 | Low |
| 2013/0193368 A1 | 8/2013 | Low |
| 2013/0221262 A1 | 8/2013 | Minor et al. |
| 2013/0283834 A1 | 10/2013 | Rao et al. |
| 2014/0020416 A1 | 1/2014 | Feiring et al. |
| 2014/0048568 A1 | 2/2014 | Demey et al. |

FOREIGN PATENT DOCUMENTS

| | | |
|---|---|---|
| DE | 19860969 | 3/2006 |
| EP | 0272919 B1 | 4/1992 |
| EP | 0684038 A2 | 11/1995 |
| EP | 1095959 A2 | 5/2001 |
| EP | 0674899 B1 | 8/2001 |
| EP | 1183003 | 3/2002 |
| EP | 1244423 | 10/2002 |
| EP | 1535860 | 6/2005 |
| EP | 1563829 | 8/2005 |
| EP | 1377268 B1 | 8/2007 |
| EP | 2 301 516 A2 | 3/2011 |
| EP | 2349185 | 8/2011 |
| EP | 1858485 B1 | 9/2013 |
| FR | 2705323 | 11/1994 |
| FR | 2814727 | 4/2002 |
| FR | 2842180 | 1/2004 |
| GB | 2296189 A | 6/1996 |
| GB | 2322847 A | 9/1998 |
| GB | 2323351 A | 9/1998 |
| GB | 2430188 A | 3/2007 |
| GB | 2440258 A | 1/2008 |
| GB | 2456028 | 7/2009 |
| GB | 2477865 A | 8/2011 |
| JP | 08-040474 | 2/1996 |
| JP | 2000-219505 | 8/2000 |
| JP | 2001-220135 | 8/2001 |
| JP | 2004-215425 | 7/2004 |
| JP | 2004-315425 A | 11/2004 |
| JP | 2006-001763 | 1/2006 |
| JP | 2006-111350 | 4/2006 |
| JP | 2006-232674 | 9/2006 |
| JP | 2009-102271 | 5/2009 |

(56) References Cited

FOREIGN PATENT DOCUMENTS

| | | |
|---|---|---|
| JP | 2010-208675 | 9/2010 |
| JP | 2011-126862 | 6/2011 |
| JP | 2011-184585 | 9/2011 |
| WO | 94/24995 A1 | 11/1994 |
| WO | 96/04884 A1 | 2/1996 |
| WO | 97/16161 | 5/1997 |
| WO | 97/16162 | 5/1997 |
| WO | 99/50156 A1 | 10/1999 |
| WO | 00/44339 A1 | 8/2000 |
| WO | 01/47476 | 7/2001 |
| WO | 02/069924 A1 | 9/2002 |
| WO | 03/092642 | 11/2003 |
| WO | 2004/039344 A1 | 5/2004 |
| WO | 2008/025524 A2 | 3/2008 |
| WO | 2008/027512 A2 | 3/2008 |
| WO | 2008/027513 A2 | 3/2008 |
| WO | 2008/027516 A1 | 3/2008 |
| WO | 2008/027595 A1 | 3/2008 |
| WO | 2009/039565 A1 | 4/2009 |
| WO | 2009/101000 | 8/2009 |
| WO | 2010/009977 A2 | 1/2010 |
| WO | 2010-035701 | 4/2010 |
| WO | 2010/089314 A1 | 8/2010 |
| WO | 2010/145919 A2 | 12/2010 |
| WO | 2010/145921 | 12/2010 |
| WO | 2012/010684 | 1/2012 |
| WO | 2012/024290 A1 | 2/2012 |
| WO | 2012/085055 | 6/2012 |

OTHER PUBLICATIONS

U.S. Appl. No. 14/026,434, filed Sep. 13, 2013, Swaile et al.
U.S. Appl. No. 14/074,516, filed Nov. 7, 2013, Smith et al.
U.S. Appl. No. 61/789,480, filed Mar. 15, 2013, Swaile.
U.S. Appl. No. 61/846,951, filed Jul. 16, 2013, Menon et al.
U.S. Appl. No. 61/847,047, filed Jul. 16, 2013, Menon et al.
U.S. Appl. No. 61/847,059, filed Jul. 16, 2013, Menon et al.
U.S. Appl. No. 61/847,067, filed Jul. 16, 2013, Swaile et al.
U.S. Appl. No. 61/929,883, filed Jan. 21, 2014, Swaile.
U.S. Appl. No. 14/090,175, filed Nov. 26, 2013, Menon et al.

* cited by examiner

AEROSOL ANTIPERSPIRANT COMPOSITIONS, PRODUCTS AND METHODS

TECHNICAL FIELD

One aspect of the invention relates generally to aerosol antiperspirant compositions. Another aspect of the invention relates generally to aerosol antiperspirant products containing an antiperspirant composition and a propellant. Yet another aspect of the invention relates generally to methods of using aerosol antiperspirant products.

BACKGROUND

Body odor may be generated in the area under the arms due to a high concentration of sweat glands. While perspiration is odorless, it contains natural oils that can be nutrient source for bacteria living on the skin. These bacteria interact with the natural oils, converting them into odor producing compounds. Antiperspirant compositions contain an active, such as an aluminum salt, that reacts with the electrolytes in perspiration to form a plug in the ducts of sweat glands. The plugs prevent perspiration from exiting the duct, thereby depriving the bacteria of water and a food source. Antiperspirant compositions may be applied to the skin in either a contact type product form, e.g., a stick or roll-on, or non-contact type product form, such as an aerosol spray. Aerosol spray devices that dispense an antiperspirant composition are known in the art. Various examples are described in U.S. Pat. No. 4,152,416; U.S. Pat. No. 4,806,338; U.S. Pat. No. 4,840,786; U.S. Pat. No. 4,904,463; U.S. Pat. No. 4,935,224; U.S. Pat. No. 5,298,236; U.S. Pat. No. 5,605,682; U.S. Pat. No. 5,814,309; U.S. Pat. No. 7,815,899; EP 674,899; WO 96/04884; WO 2004/014330; and WO 2007/001842.

Many aerosol antiperspirant users often desire a product that minimizes the appearance of residue on the skin, has a dry rather than wet feel, has rapid perceived drying, is not sticky, provides a cool/fresh feeling at time of application, provides long lasting wetness and/or odor protection, is provided in a form factor that is easily portable in purses or small bags (as some users may apply the antiperspirant composition more than once a day) and minimizes the gassy cloud that forms during dispensing. While the relative importance/desirability of these characteristics may vary by geographical region and gender and not all users desire all or the same set of characteristics, there appears to be a generally universal desire among aerosol antiperspirant users for one or more of a dry rather than wet feel, minimizing the appearance of residue and providing long lasting wetness/odor protection or efficacy.

While some currently marketed aerosol spray devices may provide at least some of these characteristics to varying degrees, there are often tradeoffs involved. For example, some currently available aerosol antiperspirant spray devices have relatively high propellant concentrations (e.g., greater than 75% and often greater than 80%). A high propellant concentration dilutes the antiperspirant composition, which in turn may help reduce the risk of clogging. However, a high propellant concentration may also produce a large volume of gas upon exiting the spray device resulting in a gassy cloud and/or a turbulent spray. Deposition efficiency (e.g., the amount of antiperspirant active and/or fragrance deposited on skin compared to the amount dispensed) may in turn be reduced due to the large amount of antiperspirant active and/or fragrance lost to the environment via the gassy cloud rather than deposited on the skin.

In addition, these spray devices are typically large (greater than 150 ml) in order to accommodate the high propellant concentration and large amount of antiperspirant composition, resulting in spray devices that may be more difficult to carry in small purses and the like. A high propellant concentration may also result in solubilization of liquid fragrance materials into the propellant during storage, resulting in more of the liquid fragrance material being lost to the environment with the propellant rather than deposited on the skin. Many currently available aerosol antiperspirant compositions also incorporate a volatile liquid (e.g., cyclopentasiloxane) as a carrier for the antiperspirant active. The volatile liquid evaporates following application to the skin, resulting in a dry skin feel, but sometimes leaves behind a visible residue (the antiperspirant active) that is subject to flaking and/or transfer to clothing. Flaking (or transfer) of the antiperspirant active may also reduce antiperspirant efficacy. Therefore, there is continuing desire to provide improved aerosol antiperspirant compositions and products.

SUMMARY OF THE DISCLOSURE

According to one aspect, an aerosol antiperspirant composition is provided. The aerosol antiperspirant composition includes a propellant and an antiperspirant composition. The antiperspirant composition includes one or more liquid materials, wherein the one or more liquid materials comprise one or more non-volatile silicone fluids having a concentration from 40% to about 70% by weight of the antiperspirant composition; antiperspirant active particulates having a concentration from about 16% to about 32% by weight of the antiperspirant composition; one or more non-antiperspirant active particulates that are substantially inert, wherein the one or more non-antiperspirant active particulates that are substantially inert have a concentration from 10% to 30% by weight of the antiperspirant composition; and wherein the antiperspirant composition has a total particulate concentration from 30% to about 60% by weight of the antiperspirant composition.

BRIEF DESCRIPTION OF THE DRAWINGS

While the specification concludes with claims, it is believed that the same will be better understood from the following description taken in conjunction with the accompanying drawings wherein like numbers illustrate like elements throughout the views and in which:

DETAILED DESCRIPTION

Figure 1:
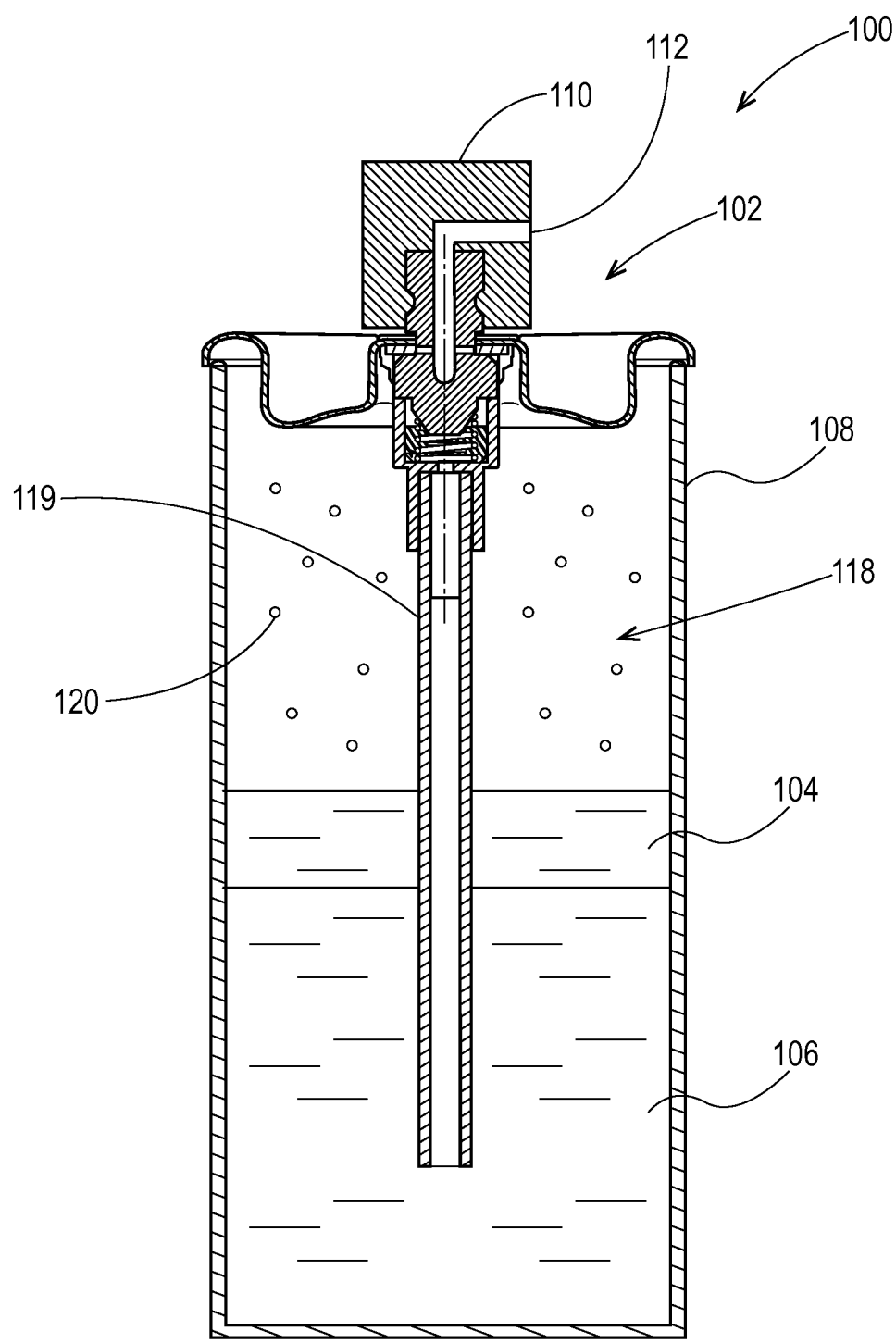
FIG. 1 is a partial cross-sectional view of one embodiment of an antiperspirant product made according to the teachings herein.

An antiperspirant composition and/or antiperspirant product may comprise, consist essentially of, or consist of, various combinations of the materials, features, structures, and/or characteristics described herein. All measurements made are at standard ambient conditions (e.g., 25° C. and absolute pressure of 101 kPA), unless otherwise specified.

Reference within the specification to "embodiment(s)" or the like means that a particular material, feature, structure and/or characteristic described in connection with the embodiment is included in at least one embodiment, but it does not mean that all embodiments incorporate the material, feature, structure, and/or characteristic described. Furthermore, materials, features, structures and/or characteristics may be combined in any suitable manner across different embodiments and materials, features, structures and/or characteristics may be omitted or substituted from what is described.

The term "anhydrous" as used herein in connection with an antiperspirant composition refers to an antiperspirant composition that is substantially or completely free of added water, meaning water added as a separate ingredient to the antiperspirant composition. An anhydrous antiperspirant composition may contain up to 10%, 8%, 6%, 4%, 2%, 15, or 0.5% water by weight of the antiperspirant composition that is bound with an ingredient (e.g., antiperspirant active, tapioca starch, etc.) added to the antiperspirant composition.

The term "aerosol antiperspirant product" refers to the combination of an aerosol antiperspirant product container, an antiperspirant composition, and a liquid propellant stored in the aerosol antiperspirant product container.

The term "aerosol antiperspirant product container" and derivatives thereof refers to the complete aerosol package intended to store and dispense an antiperspirant composition and liquid propellant. An aerosol antiperspirant product container may typically comprise at least one reservoir for storing an antiperspirant composition and liquid propellant, a valve for controlling flow of the antiperspirant composition and liquid propellant mixture, and an actuator by which a user can actuate the valve.

The term "antiperspirant composition" refers to the combination of one or more liquid materials, antiperspirant actives and other materials that are flowable and intended to be sprayed onto skin, exclusive of the propellant. The antiperspirant composition may be provided in the form of a liquid dispersion (including suspensions and colloids). An antiperspirant composition also includes a combination of the one or more liquid materials, antiperspirant actives and other materials, wherein one or more particulates (e.g., particulates of an antiperspirant active) or other materials have undergone settling from one or more of the liquid materials.

The term "bulking or suspending material" refers to a material which is intended to reduce settling of an antiperspirant active (and/or other particulates) from a liquid material and/or reduce the severity of particulate caking post settling. Some non-limiting examples of common bulking or suspending agents include, but are not limited to, colloidal silicas and clays.

The term "clogging" refers to either a blocked passage, orifice, hole or other opening resulting in little or no mass flow out of a product container when the actuator is activated or a valve stuck at least partially open from accumulated antiperspirant composition, resulting in semi continuous or continuous leakage of the antiperspirant composition and/or propellant from a product container.

The term "controlling orifice" refers to the orifice(s), hole(s) or other opening(s) which principally control or meter the mass flow of the antiperspirant composition/liquid propellant mixture thru the product container. In some instances, the controlling orifice may comprise a plurality of orifices, holes or openings which are arranged in a generally parallel fashion with respect to the mass flow of the mixture and which in combination principally control or meter the mass flow thru the product container. The controlling orifice is typically the smallest opening(s) thru which the mixture of liquid propellant and antiperspirant composition flows. The controlling orifice may sometimes be the valve opening.

The term "deposition efficiency" refers to the percentage of a material (e.g., antiperspirant active, fragrance material, antiperspirant composition, etc.) that is deposited on a target surface compared to the amount of the material that exits an aerosol antiperspirant product.

The term "excipient particulate" and "excipient particulate material" and "particulates of an excipient material" refer to a particulate material that is substantially inert with respect to itself and/or an antiperspirant active, meaning there are no significant particle to particle interactions with respect to itself and/or the antiperspirant active when present in an antiperspirant composition. Excipient particulates exclude clays and silicas added to an antiperspirant composition as bulking or suspending materials, as these particles can exhibit strong particle to particle interactions.

The term "gum" is used to refer to a material that has a viscosity within the range from about 100,000 to about 100 million centistokes at 25° C. and which slowly flowable, as opposed to a rigid solid, which is not flowable, or a liquid, which is too flowable.

The term "life cycle" refers to the total amount of dispensing time provided by an aerosol antiperspirant product.

The term "particulate", as used herein, refers to a material that is solid or hollow and which is substantially or completely insoluble in the liquid materials of an antiperspirant composition.

The term "product efficacy" refers to amount of wetness protection provided by application of an aerosol antiperspirant composition from an aerosol antiperspirant product to an axillia.

The terms "propellant" and "liquid propellant" refer to the liquid propellant added to an aerosol antiperspirant container or that is stored within an aerosol antiperspirant container, exclusive of liquid materials that are miscible with the liquid propellant and exclusive of the gaseous propellant in the head space of a container (which tends to be negligible).

The term "substantially free" refers to an amount of a material that is less than 1%, 0.5%, 0.25%, 0.1%, 0.05%, 0.01%, or 0.001% by weight of an antiperspirant composition.

The term "total fill" refers to the total amount of materials added to or stored within a reservoir(s) of an aerosol antiperspirant product container. Total fill includes the total amount of liquid propellant and antiperspirant composition stored within the aerosol antiperspirant product after completion of filling and prior to the first use of the product.

Various combinations of liquid propellants, antiperspirant compositions, aerosol antiperspirant product containers, and aerosol antiperspirant products, and their methods of making and use, will now be described.

I. Liquid Propellants

An aerosol antiperspirant product comprises a liquid propellant stored in at least one reservoir of the product container. The liquid propellant may be stored in the same reservoir as an antiperspirant composition or a separate reservoir. The propellant may be provided as a pressurized, liquefied gas which is miscible in a non-volatile silicone fluid of the antiperspirant composition. The propellant is utilized to drive the antiperspirant composition out of the product container during use and to assist with atomizing the antiperspirant composition as it exits the product container via the vaporization and expansion of the liquid propellant.

The liquid propellant concentration of the aerosol antiperspirant product may impact the mass flow rate of the antiperspirant composition there from. The mass flow rate of the antiperspirant composition refers to that portion of the total mass flow rate of the liquid propellant/antiperspirant composition mixture that is attributable to the antiperspirant composition. The antiperspirant composition mass flow rate generally increases as propellant concentration decreases (assuming all other variables, such as pressure within the container, remain unchanged), because the ratio of antiperspirant composition to liquid propellant in the total mass flow of the mixture increases with decreasing propellant concentration. This effect is most pronounced for hydrocarbon propellants (e.g., butane, isobutene, propane, etc.), which may have a density below that of the antiperspirant composition resulting in a larger volume fraction of the total mass flow. An increase in antiperspirant composition mass flow may lead to an increase in the amount of antiperspirant composition deposited on skin per use. Decreasing liquid propellant concentration may also reduce the amount of antiperspirant composition lost to the environment in the form of a gassy cloud, thereby further increasing the amount deposited on skin per use. Increasing the amount of antiperspirant composition deposited on skin may increase product efficacy/wetness protection, as more antiperspirant active is delivered to the skin.

A reduction in the amount of free fragrance material solubilizing into the liquid propellant is another benefit that may result from decreasing propellant concentration. As liquid propellant concentration decreases, the amount of free fragrance material that may solubilize into the liquid propellant during storage decreases due to the lower amount of liquid propellant in the product container. Decreasing the amount of free fragrance material solubilizing into the liquid propellant means less fragrance material may be lost to the environment as the liquid propellant turns to gas, and therefore more free fragrance material may be deposited on the skin as part of the antiperspirant composition.

While reducing liquid propellant concentration may enable increasing the amount antiperspirant composition and/or free fragrance material deposited on skin per use, there are a number of confounding tradeoffs that may come into play. For example, increasing the antiperspirant composition mass flow rate too much may negatively impact skin feel (e.g., lead to a wet or sticky feel from the presence of too much antiperspirant active on skin), increase the risk of clogging within the small controlling orifices of the product container, increase the likelihood of a visible residue, and/or diminish the cool/fresh feeling at time of application due to less liquid propellant depositing on the skin and subsequently vaporizing there from. Thus, there are a number of challenges to address when reducing propellant concentration in an aerosol antiperspirant product.

It is believed that liquid propellant concentrations less than 30% by weight of the total fill of the product container may result in too high of a mass flow rate of the antiperspirant composition. While reducing the controlling orifice size/area may help offset some of the antiperspirant composition mass flow rate increase from reducing propellant concentration, propellant concentrations less than 30% may require orifice sizes that are so small that they may become susceptible to clogging (the risk of which also increases as propellant decreases and as particulate concentration increases) and/or which may be more challenging to manufacture in a cost effective manner for commercial products. It is also believed that liquid propellant concentrations greater than 65% by weight of the total fill of the product container may result in high solubilization of free fragrance materials in the liquid propellant and/or otherwise lead to a significant reduction in the deposition efficiency of a free fragrance material.

The liquid propellant may have a concentration from about 30%, 32%, 34% 36%, 38%, 40%, or 42% to about 65%, 60%, 54%, 52%, 50%, 48%, 46%, 44%, or 42% by weight of the total fill of materials (i.e., propellant and antiperspirant composition) stored within the aerosol antiperspirant container. The amount of liquid propellant (in grams) stored within an aerosol antiperspirant container may be from about 4 g, 6 g, 8 g, 10 g to about 50 g, 25 g, 20 g, or 15 g. The volume of liquid propellant stored within the aerosol antiperspirant container may be from about 10 ml, 20 ml, 30 ml, or 40 ml to about 100 ml, 80 ml, 70 ml, 60 ml, or 50 ml.

A wide variety of liquid propellants may be used with the products and antiperspirant compositions described herein. The liquid propellants useful in the present invention typically have a boiling point (at atmospheric pressure) within the range of from about $-45°$ C. to about $5°$ C. The propellants are preferably liquefied when packaged in the container under pressure. The rapid expansion of the propellant upon leaving the product container aids in the atomization of the antiperspirant composition. Suitable propellants may include chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 difluoroethane). Some aerosol antiperspirant products may incorporate an A-31 or A-46 propellant.

Utilizing a propellant having boiling point less than $5°$ C. as the primary propellant can be beneficial, because these propellants quickly expand to form a gas after leaving the product container thereby creating a fine spray and higher forces (compared to higher boiling point propellants) to deliver the antiperspirant composition to the target skin surface. However, an aerosol antiperspirant product utilizing a low propellant concentration can also suffer from a diminished cool/fresh sensation at the time of application because less liquid propellant is reaching the skin and subsequently vaporizing thereat. Thus, it may be desirable to provide an aerosol antiperspirant product comprising a mixture of propellants having different boiling points. Combining a primary propellant(s) having a boiling point less than 5 C with a secondary propellant(s) having a boiling point above 5° C. may increase the likelihood of more liquid propellant reaching the skin. This in turn may enhance the cool/fresh sensation at time of application due to the vaporization of the additional liquid propellant (e.g., the secondary propellant) from the skin. The secondary propellant may have a concentration from about 1% to about 20%, or from about 1% to about 15%, or from about 2% to about 10% by weight of the total fill of materials in the product. The secondary propellant(s) may have a boiling point from about 5° C., 10° C., 15° C., 20° C., or 25° C. to about 40° C., 35° C., or 30° C. In some embodiments, the secondary propellant(s) may have a boiling point greater than room temperature, or from 25° C. to 40° C., which can further increase the likelihood that the secondary propellant(s) reaches the skin and vaporizes thereat. Two non-limiting exemplary propellants suitable for use as secondary propellants include pentane and isopentane, although other propellants having boiling points within the ranges described herein may also be used.

The propellant may provide a pressure within a product container from about 60 kPa to about 500 kPA, or 200 kPa to about 400 kPa, or 200 kPa to about 350 kPa at 25° C. The propellant may provide a pressure within a product container from about 100 kPa to about 1100 kPA, or 200 kPa to about 1,100 kPa, or 400 kPa to about 900 kPa at 55° C.

II. Aerosol Antiperspirant Compositions

The antiperspirant compositions described herein comprise one or more non-volatile silicone fluids and one or more particulate antiperspirant actives. An antiperspirant composition may further comprise one or more non-antiperspirant active particulate materials, preferably one or more excipient particulate materials and more preferably one or more hydrophilic excipient particulate materials. An antiperspirant composition may optionally comprise one or more silicone gum materials, one or more suspending or bulking agents, one or more fragrance materials, and mixtures thereof. Other ingredients may also be optionally included, as known in the art. An antiperspirant composition is preferably anhydrous, as too much added water may result in several deleterious effects such as: 1) increasing the propensity for antiperspirant active particulates to agglomerate (thereby increasing the propensity for clogging), and 2) reducing dry feel on skin.

Since an aerosol antiperspirant composition should be flowable so that it may be sprayed from a product container and provide the desired skin feel characteristics, an aerosol antiperspirant composition may be devoid of agents in sufficient concentrations that a stick-type rheology is provided. Some common agents which may be excluded in meaningful amounts include hydrogenated castor oil, solid paraffins, silicone waxes, and mixtures thereof.

A flowable aerosol antiperspirant composition may have an average viscosity from about 1,000 centipose, 2,000 centipose, or 3,000 centipose to about 7,000, or 5,000 centipose or 4,000 centipose at 25° C. A viscosity lower than 1,000 centipose may lead to an aerosol antiperspirant composition, which when spayed, results in a runny or drippy effect on skin that may be perceived by a user as wet rather than dry. While roll-on type antiperspirant compositions may have viscosities below 1,000 centipose, the runny or drippy effect may be managed in roll-on type products by a roller ball which applies a thin film of the antiperspirant composition compared to an aerosol antiperspirant composition which is applied in a more uncontrolled manner.

An aerosol antiperspirant product may comprise from about 40%, 45%, 50%, or 55% to about 70%, 65%, or 60% by weight of the total fill of materials of an antiperspirant composition. An aerosol antiperspirant product may comprise from about 4 g, 6 g, 8 g, 10 g, 12 g, 14 g, or 16 g to about 70 g, 50 g, 40 g, 30 g, or 20 g of an antiperspirant composition. The antiperspirant composition concentration and/or mass of an already filled container (assuming it is not known how much was added to the container) may be measured by a variety of means known in the art.

As previously discussed, lower propellant concentrations may increase the mass flow rate of the antiperspirant composition, thereby increasing the deposition efficiency and/or amount of antiperspirant active deposited per use, which in turn may increase product efficacy/wetness protection if the active remains substantive on the skin. However, lower propellant concentrations may increase the risk of clogging, as less propellant is available for expansion and purging of the valve and actuator passages/openings of the antiperspirant composition. Any antiperspirant composition that remains within the product container downstream of or within the valve is subject to drying, particularly when a volatile liquid carrier is used. Incorporating a non-volatile silicone fluid in the antiperspirant composition is one means for minimizing drying within the product container post use, thereby reducing the risk of clogging of the product container. In addition, incorporating a non-volatile silicone fluid may increase the substantivity of the antiperspirant composition on skin, thereby potentially increasing product efficacy as the antiperspirant composition may form a film that more readily adheres to skin rather than flaking off.

A. Non-Volatile Silicone Fluids

The antiperspirant compositions comprise at least one non-volatile, silicone fluid as a carrier for the one or more antiperspirant actives and/or other components of the antiperspirant composition. As used herein, the term "non-volatile" refers to a material that has a boiling point above 250° C. (at atmospheric pressure) and/or a vapor pressure below 0.1 mm Hg at 25° C. The non-volatile, silicone fluid may comprise a mixture of silicone components in addition to other constituents, although non-volatile silicone components should comprise the bulk of the fluid. An aerosol antiperspirant composition may comprise a plurality of non-volatile, silicone fluids.

The total concentration of non-volatile, silicone fluids may be from about 40%, 45%, 50% to about 70%, 65%, 60%, or 55% by weight of an antiperspirant composition. In some embodiments, the total concentration of non-volatile, silicone fluids may be from about 45% to about 55% by weight of an antiperspirant composition. The liquid materials of the antiperspirant composition may consist essentially of or are primarily formed from one or more non-volatile, silicone fluid(s). It is believed that a concentration of the one or more non-volatile silicone fluids of less than 40% by weight of the antiperspirant composition in combination with a low propellant concentration may be insufficient to prevent eventual drying (and attendant clogging) of the antiperspirant composition in between uses, particularly where the antiperspirant composition comprises a high concentration of particulates. In addition, lower concentrations of non-volatile silicone fluid(s) may reduce the ability of the fluid to minimize the appearance of residue for antiperspirant compositions that comprises high concentrations of particulates. It is also believed that a concentration of the one or more non-volatile silicone fluids greater than 70% by weight of the antiperspirant composition may result in too low of a concentration of particulates compared to the amount of liquid materials to effectively provide a dry feel of the composition during use.

Some non-volatile, silicone fluids that may be used include, but are not limited to, polyalkyl siloxanes, polyalkylaryl siloxanes, and polyether siloxane copolymers, and mixtures thereof. Some preferred non-volatile silicone fluids may be linear polyalkyl siloxanes, especially polydimethyl siloxanes (e.g., dimethicone) having the molecular formula of $(C_2H_6OSi)_n$. These siloxanes are available, for example, from Momentive Performance Materials, Inc. (Ohio, USA) under the tradename Element 14 PDMS (viscosity oil). Silicones Fluids from Dow Corning Corporation (Midland, Mich., USA) available under the trade name Dow Corning 200 Fluid series (e.g., 10 to 350 cps).

Other non-volatile silicone fluids that can be used include polymethylphenylsiloxanes. These siloxanes are available, for example, from the General Electric Company as SF 1075 methyl phenyl fluid or from Dow Corning as 556 Fluid. A polyether siloxane copolymer that may be used is, for example, a dimethyl polyoxyalkylene ether copolymer fluid. Such copolymers are available, for example, from the General Electric Company as SF-1066 organosilicone surfactant.

The non-volatile, silicone fluid may have an average viscosity from about 5 centistokes, 10 centistokes, 20 centistokes, or 50 centistokes to about 900 centistokes, 500 centistokes, 350 centistokes, 100 centistokes or 50 centistokes at 25° C. In some specific embodiments, the silicone fluid may have a viscosity about 50 cs. At less than 5 centistokes, the silicone fluid may become volatile and at viscosities greater than 900 centistokes, the antiperspirant composition may be too thick to atomize. While the non-volatile silicone fluid may have an average viscosity within the described ranges, it will be appreciated that individual silicone components of the fluid may have viscosities outside of the described ranges. The viscosity of the non-volatile silicone fluid may be selected to provide a desired overall viscosity of the antiperspirant composition. In some specific embodiments, the viscosity of the non-volatile silicone fluid is from about 10 centistokes to about 100 centistokes.

B. Other Liquid Materials

While it may be desirable for the liquid materials of the antiperspirant composition to consist essentially of or be primarily formed from non-volatile silicone fluids, it is contemplated that other liquid materials may be included in the antiperspirant composition at lower concentrations. For example, liquid fragrance materials and/or a silicone gum may be optionally included in an antiperspirant composition. The liquid materials of the antiperspirant composition may comprise less than 30%, 20%, 10%, or less than 5% by weight of liquids other than non-volatile, silicone fluids. Said in another way, the liquid materials of the antiperspirant composition may comprise more than 70%, 75%, 80%, 85%, 90% or about 100% by weight of non-volatile silicone fluids.

It is believed that an antiperspirant composition whose liquid materials comprise too much of a volatile silicone fluid may lead to an increased propensity for the appearance of a residue due to the evaporation of the volatile silicone fluid. An antiperspirant composition may comprise less than 10%, 5%, 1%, or 0.5% by weight of a volatile silicone fluid. An antiperspirant composition may be substantially or completely free of a non-volatile silicone fluid.

An antiperspirant composition may optionally comprise one or more silicone gums. A silicone gum may be added to an antiperspirant composition to further increase substantivity of the antiperspirant composition and/or increase the drop size of the aerosol spray particles. However, formulating an aerosol antiperspirant composition with a silicone gum in combination with relatively high concentrations of a non-volatile silicone fluid and/or relatively high concentrations of total particulates may involve a number of tradeoffs. For example, too much of a silicone gum may dramatically increase viscosity of the antiperspirant composition and the risk of clogging of the container actuator and/or valve, particularly where there is already a relatively high concentration of total particulates. Still further, too much of a silicone gum may reduce the diameter of the spray making it more difficult for a user to achieve complete coverage of an axillia (typically a 7.5 cm×12.5 cm area) during application as well as potentially creating regions of high antiperspirant composition dosage, thereby negatively impacting skin feel.

Given the challenges associated with incorporating a silicone gum in an aerosol antiperspirant product comprising a low propellant concentration and high concentration of a non-volatile silicone fluid, an antiperspirant composition may be substantially or completely free of silicone gum materials. When inclusion of a silicone gum is desirable, an antiperspirant composition may have a concentration from about 0.05% or 0.075% to about 0.5%, 0.4%, 0.3%, or 0.2% of a silicone gum by weight of the antiperspirant composition. The silicone gum material may have a viscosity from about 100,000 centistokes to about 10,000,000 centistokes at 25° C.

If a silicone gum is included, any silicone gum having a viscosity within the ranges described herein may be used, provided it is soluble in the liquid carrier, propellant or a combination thereof of the antiperspirant composition. Some suitable silicone gums include silicone polymers of the dimethyl polysiloxane type, which may have other groups attached, such as phenyl, vinyl, cyano, or acrylic, but the methyl groups should be in a major proportion. Silicone polymers having a viscosity below about 100,000 centistokes (molecular weight below about 100,000) at 25° C. are not considered silicone gums here but are rather, typically, considered a silicone fluid. One non-limiting example of silicone gum suitable for use is a silicone/gum fluid blend comprising a dimethiconol gum having a molecular weight form about 200,000 to 4,000,000 along with a silicone fluid carrier with a viscosity from about 0.65 to 100 mm$^2$ s$^{-1}$. An example of this silicone/gum blend is available from Dow Corning, Corp. of Michigan, USA under the trade name DC-1503 Fluid (88% dimethicone fluid/12% dimethiconol). Other silicone gums materials include SF1236 Dimethicone, SF1276 Dimethicone, and CF1251 Dimethicone available from Momentive Performance Materials, Inc. of NY, USA.

An antiperspirant composition may optionally comprise one or more free fragrance materials. Free fragrance materials are typically liquids, which may contribute to the total amount of liquid materials in an antiperspirant composition. As used herein the term free fragrance material means a fragrance material that is not encapsulated, such as, for example, a mixture of perfume or aromatic components that are optionally mixed with a suitable solvent, diluent or carrier. Some suitable solvents, diluents or carriers for the perfume components may include ethanol, isopropanol, diethylene glycol monoethyl ether, dipropylene glycol, diethyl phthalate, triethyl citrate, and mixtures thereof. An antiperspirant composition may comprise from about 0.5%, 0.75% or 1% to about 4%, 3%, 2%, or 1.5% of a free fragrance material. An aerosol antiperspirant product may contain from about 0.5 g, 0.75 g, or 1 g to about 3 g, 2 g, or 1.5 g of free fragrance materials.

A perfume component may be any natural or synthetic perfume component known to one skilled in the art of creating fragrances including, but not limited to, essential oils, citrus oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Some non-limiting examples of perfume components include: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenyl-carbinyl acetate, p-tert.butyl-cyclohexyl acetate, isononyl acetate, vetiveryl acetate, vetiverol, alpha-n-amylcinammic aldehyde, alpha-hexylcinammic aldehyde, 2-methyl-3-(p-tert.butylphenyl)-propanol, 2-methyl-3-(p-isopropylphenyl)-propanal, 3-(p-tert.butylphenyl)-propanal, tricyclodecanyl acetate, tricyclodecanyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyltetrahydropyran, methyldihydrojasmonate, 2-n-heptylcyclopentanone, 3-methyl-2-pentylcyclopentanone, n-decanal, 9-decenol-1, phenoxyethyl isobutyrate, phenyl-acetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylionones, irones, cis-3-hexenol and esters thereof, indane musk fragrances, tetralin musk fragrances, isochroman musk fragrances, macrocyclic ketones, macrolactone musk fragrances, ethylene brassylate, aromatic nitro-musk fragrances. Some perfume components are also described in Arctander, Perfume and Flavour Chemicals (Aroma Chemicals), Vol. I and II (1969) and Arctander, Perfume and Flavour Materials of Natural Origin (1960).

C. Particulate Materials

While the combination of low propellant concentration and a high concentration of non-volatile silicone fluids may provide a number of benefits, this combination may also result in a number of tradeoffs. For example, higher antiperspirant active deposition (due to a lower propellant concentration) in combination with a high concentration of a non-volatile silicone fluid may result in a wet and/or sticky skin feel. In addition, a non-volatile silicone fluid may tend to impede release of the antiperspirant active more so than a volatile liquid carrier, as a volatile liquid carrier eventually evaporates leaving behind the antiperspirant active and the other non-volatile components, which are easily wetted by perspiration thereby releasing the antiperspirant active. In contrast, non-volatile silicones do not evaporate as easily and tend to be hydrophobic, thereby potentially decreasing antiperspirant active release.

Incorporating a high concentration of particulates is one means identified for improving dry skin feel in an antiperspirant composition comprising a high concentration of a non-volatile liquid material. It is believed, however, that too low of an amount of particulates relative to the amount of non-volatile liquid materials may lead to an insufficient improvement in dry skin feel. Conversely, it is believed that too high of an amount may lead to an unacceptable appearance of residue, because there is too little non-volatile silicone fluid to act as a masking agent for the high amount of particulates. Surprisingly, it may be possible to increase the total concentration of particulates to improve skin feel to an acceptable level (in a composition comprising a high concentration of non-volatile silicones) while still minimizing the appearance of a residue by balancing the total amount of non-volatile liquids to the total amount of particulates. The type and concentration of particulates may also affect the antiperspirant active release, which are additional formulation design considerations.

It is believed that an aerosol antiperspirant composition comprising a total non-volatile liquid material to total particulate material ratio (L/P ratio) from about 0.6, 0.8, 1, 1.2, or 1.4 to about 1.6 may balance the tradeoff between enough particulates to provide acceptable skin feel while minimizing the appearance of residue. These ratios may be particularly beneficial for an aerosol antiperspirant product having an antiperspirant composition mass flow rate less than 0.3 g/sec, 0.2 g/sec, or 0.15 g/sec, as these L/P ratios may not be able to compensate for undesirable skin feel induced by higher mass flow rates. In some specific embodiments, it may be desirable to utilize an L/P ratio from about 0.6 to about 1.2 or from about 1 to about 1.2 when high concentrations of a low viscosity (e.g., 10 centistokes to 100 centistokes) non-silicone fluid are incorporated in an antiperspirant composition in order to achieve an appropriate antiperspirant composition viscosity. It is further believed that L/P ratios from about 0.8 to about 1.4 may be particularly preferred for balancing the aforementioned tradeoff(s). An antiperspirant composition may have a total particulate concentration from about 30%, 35%, or 40% to about 60%, 55%, or 50% by weight of the antiperspirant composition, in keeping with the total liquid to total particulate (L/P) ratios previously described.

While the antiperspirant composition may comprise a variety of particulate materials, it is believed that the type (e.g., hydrophilic v. hydrophobic) and concentrations of particulate materials included in an antiperspirant composition may impact skin feel, release of the antiperspirant active, and the propensity for clogging of the product container. For example, too much antiperspirant active may result in a wet or sticky skin feel due to the propensity of antiperspirant actives to become sticky when hydrated (e.g., by perspiration) even within the L/P ratios previously described. In addition, too much of a hydrophobic particulate material may reduce release of the antiperspirant active from the composition. Conversely, inclusion of a hydrophilic particulate material may advantageously aid release of the antiperspirant active, which may be beneficial in a composition comprising a high concentration of a non-volatile silicone fluid. Further, too much of a bulking or suspending material may lead to an increased risk of clogging, particularly if smaller controlling orifices are utilized in a low propellant product. Therefore, it may be desirable to balance these and other design considerations when incorporating particulate materials in an aerosol antiperspirant composition.

Some examples of particulate materials that may be included in antiperspirant composition include but are not limited to antiperspirant actives, excipient particulates (e.g., powders such as tapioca starch, corn starch, encapsulated fragrance materials, etc.) and bulking or suspending agents (e.g., silicas or clays). Other types of particulates may also be incorporated in an antiperspirant composition.

Antiperspirant Actives

An aerosol antiperspirant composition comprises one or more antiperspirant actives. The antiperspirant active may be any particle having antiperspirant activity. An antiperspirant active may be substantially insoluble in the antiperspirant composition. Since the amount of an antiperspirant active may significantly impact skin feel, an antiperspirant composition may comprise from about 16%, 18%, 20%, 22%, or 24% to about 34%, 32%, 30%, 28%, or 26% by weight of an antiperspirant active. These antiperspirant active concentrations are the anhydrous amount that is added. The antiperspirant active may represent the highest concentration of particulate materials in the antiperspirant composition. For example, the antiperspirant active (on an anhydrous basis) may comprise from about 50% to about 80%, or from about 50% to about 70%, or from about 50% to about 60% of the total particulate materials in the antiperspirant composition. The balance of the total particulate concentration comprises non-antiperspirant active particulates. An aerosol antiperspirant product may contain from about 1 g to about 20 g, or from about 2 g to about 15 g, or from about 4 g to about 10 g of an antiperspirant active.

Some examples of suitable antiperspirant actives include astringent metallic salts, particularly including the inorganic and organic salts of aluminum. Some exemplary aluminum salts that can be used include aluminum chloride and the aluminum hydroxyhalides having the general formula $Al_2(OH)_aQ_bXH_2O$ where Q is chloride, bromide, or iodide (preferably chloride), a is from about 2 to about 5, and a+b=about 6, and a and b do not need to be integers, and where X is from about 1 to about 6, and X does not need to be an integer. Particularly preferred are the aluminum chlorhydroxides referred to as "5/6 basic chlorhydroxide" wherein "a" is 5 and "2/3 basic chlorhydroxide" wherein "a" is 4. Aluminum salts of this type can be prepared in the manner described more fully in U.S. Pat. Nos. 3,887,692; 3,904,741; and 4,359,456. Preferred compounds include the 5/6 basic aluminum salts of the empirical formula $Al_2(OH)_5Cl\cdot2H_2O$; mixtures of $AlCl_3\cdot6H_2O$ and $Al_2(OH)5Cl_2H_2O$ with aluminum chloride to aluminum hydroxychloride weight ratios of up to about 0.5.

Excipient Particulate Materials

Excipient particulate materials may comprise the second highest concentration of particulate materials in an aerosol antiperspirant composition. An antiperspirant composition may comprise from about 5%, 10%, or 15% to about 35%, 30%, 25% or 20% by weight of excipient particulate materials. Excipient particulate materials may comprise from about 20% to about 48%, or from about 25% to about 48%, or from about 30% to about 48% of the total particulate materials. Excipient particulate materials may be hydrophobic or hydrophilic. In some specific embodiments, the excipient materials may consist essentially of or completely of hydrophobic or hydrophilic materials. Preferably, the excipient materials consist essentially or completely of hydrophilic particulate materials.

Some non-limiting excipient particulate materials include, but are not limited to, native starches such as tapioca, corn, oat, potato and wheat starch powders, and encapsulated fragrance materials. The particulates may be hydrophilic or hydrophobically modified (the later tending to only be moderately hydrophobic). The particulates may be free flowing and may have an average particle size less than 30 microns. One excipient particulate material believed to be particularly suitable for use is a hydrophilic or hydrophobically modified tapioca starch particulate material, preferably a hydrophilic tapioca material. Tapioca is a starch which may be extracted from the cassava plant, typically from the root, which may then be processed or modified as known in the art. Tapioca starches are, advantageously, substantially non-allergenic. Tapioca starch particulates may be round to oval in shape and may have an average particle size about 20 microns, which is believed to have a positive impact on antiperspirant composition flow through the valve and actuator. One non-limiting example of a hydrophobically modified tapioca material suitable for use comprises a silicone grafted tapioca starch, which is available under the trade name Dry Flo TS from AkzoNobel of the Netherlands. The INCI name is tapioca starch polymethylsilsesquioxane and may be produced by a reaction of methyl sodium siliconate (polymethylsilsesquioxane) and tapioca starch. This silicone grafted tapioca starch is commercially available as CAS no. 68989-12-8. The silicone grafted tapioca starch can be formed using any known means, including, but not limited to those methods described in U.S. Pat. Nos. 7,375,214, 7,799,909, 6,037,466, 2,852,404, 5,672,699, and 5,776,476. Other non-limiting examples of hydrophobically modified tapioca starch materials that are suitable for use include Dry Flo AF (silicone modified starch from Akzo Nobel), Rheoplus PC 541 (Siam Modified Starch), Acistar RT starch (available from Cargill) and Lorenz 325, Lorenz 326, and Lorenz 810 (available from Lorenz of Brazil).

In some specific embodiments, the tapioca material may be hydrophilic in order to facilitate release of the antiperspirant active during use. A non-limiting example of a hydrophilic tapioca starch material suitable for use is available under the trade name Tapioca Pure available from Akzo Nobel. The tapioca starch material may have a concentration from about 2%, 4%, 6%, 8%, 10%, or 15% to about 40%, 35%, 30%, 25% or 20% by weight of the antiperspirant composition.

An antiperspirant composition may optionally comprise one or more encapsulated fragrance materials as excipient materials for masking malodors, absorbing malodors, or which otherwise provide the antiperspirant compositions with a desired aroma during use. As used herein, the phrase "encapsulated fragrance material" refers to perfume components and the carrier encapsulating the perfume components. Encapsulated fragrance materials also refer to carriers capable of absorbing a fragrance or malodor in use, such as for example an uncomplexed cyclodextrin material. The encapsulated perfume components may be released by a moisture activation mechanism whereby upon being wetted, e.g., by perspiration or other body fluids, the encapsulated perfume component is released. Alternatively or in addition thereto, the perfume components may be released by fracture of the carrier, such as by the application of pressure, a shear force, or other event which releases the perfume component due to application of a force to the carrier. Encapsulated fragrance materials may be provided in a particulate form which would be considered part of the total particulate concentration of the antiperspirant composition.

An antiperspirant composition may comprise from about 0.25% to about 5%, or from about 0.5% to 5%, or from about 0.5% to about 4% by weight of the antiperspirant composition of an encapsulated fragrance material. An aerosol antiperspirant product may contain from about 0.01 g to about 4 g, or from about 0.05 g to about 2 g, or from about 0.05 g to about 1.5 g of an encapsulated fragrance material. Examples of some carriers suitable for forming the encapsulated fragrance materials include, but are not limited to, oligosaccharides (e.g., cyclodextrins), starches, polyethylenes, polyamides, polystyrenes, polyisoprenes, polycarbonates, polyesters, polyacrylates, vinyl polymers, silicas, and aluminosilicates. Some examples of encapsulated fragrance materials are described in USPNs 2010/0104611; 2010/0104613; 2010/0104612; 2011/0269658; 2011/0269657; 2011/0268802; U.S. Pat. Nos. 5,861,144; 5,711,941; 8,147,808; and 5,861,144.

As used herein, the term "cyclodextrin" includes any of the known cyclodextrins such as unsubstituted cyclodextrins containing from six to twelve glucose units, especially alpha-cyclodextrin, beta-cyclodextrin, gamma-cyclodextrin and/or their derivatives and/or mixtures thereof. The term "uncomplexed cyclodextrin" as used herein means that the cavities within the cyclodextrin in the composition of the present invention should remain essentially unfilled prior to application to skin in order to allow the cyclodextrin to absorb various odor molecules when the composition is applied to the skin. While it is desirable that the cyclodextrins incorporated in an antiperspirant composition contain a perfume component, it is contemplated that uncomplexed cyclodextrins may be incorporated as part of the total particulate amount in some instances.

Some cyclodextrins suitable for use in the present invention include alpha-cyclodextrin, beta-cyclodextrin, gamma-cyclodextrin, their derivatives, and mixtures thereof. More preferred are beta cyclodextrin, hydroxypropyl alpha-cyclodextrin, hydroxypropyl beta-cyclodextrin, methylated-alpha-cyclodextrin or methylated-beta-cyclodextrin, and mixtures thereof. Some cyclodextrin complexes, particle sizes, and methods of formation useful herein, are disclosed in U.S. Pat. No. 5,429,628.

The encapsulated fragrance material, whatever form it takes, may comprise a wide variety of perfume components, including but not limited to volatile perfume components having a boiling point at normal pressure of less than about 260° C., more preferably less than about 250° C., and perfume components having significant low odor detection threshold, and mixtures thereof. The boiling points of many perfume components are given in, e.g., "Perfume and Flavor Chemicals (Aroma Chemicals)," Steffen Arctander, published by the author, 1969.

Bulking or Suspending Agents

An antiperspirant composition may optionally comprise one or more particulate bulking or suspending agents. The bulking or suspending agent may be hydrophobic, hydrophilic, or comprise mixtures thereof. In some specific embodiments, these materials may be hydrophilic in order to facilitate release of the antiperspirant active during use. Some examples of silica materials that may be used include, but are not limited to, colloidal silicas. Some non-limiting examples of silica materials are available from Evonik Industries under the trade names Aerosil 200SP, Aerosil 300SP, and Aerosil R972.

Some examples of clay materials that may be used at a low concentration include, but are not limited to, montmorillonite clays and hydrophobically treated montmorillonite clays. Montmorillonite clays are those which contain the mineral montmorillonite and may be characterized by a having a suspending lattice. Some examples of these clays include but are not limited to bentonites, hectorites, and colloidal magnesium aluminum silicates. Clay materials may be made hydrophobic by treatment with a cationic surfactant, such as a quaternary ammonium cationic surfactant. One example of a clay material is available from Elementis Specialities, Plc. of the UK under the trade name Bentone 38. A clay activator, such as propylene carbonate or triethyl citrate, may also be included in the antiperspirant composition.

III. Aerosol Antiperspirant Containers and Products

Figure 2:
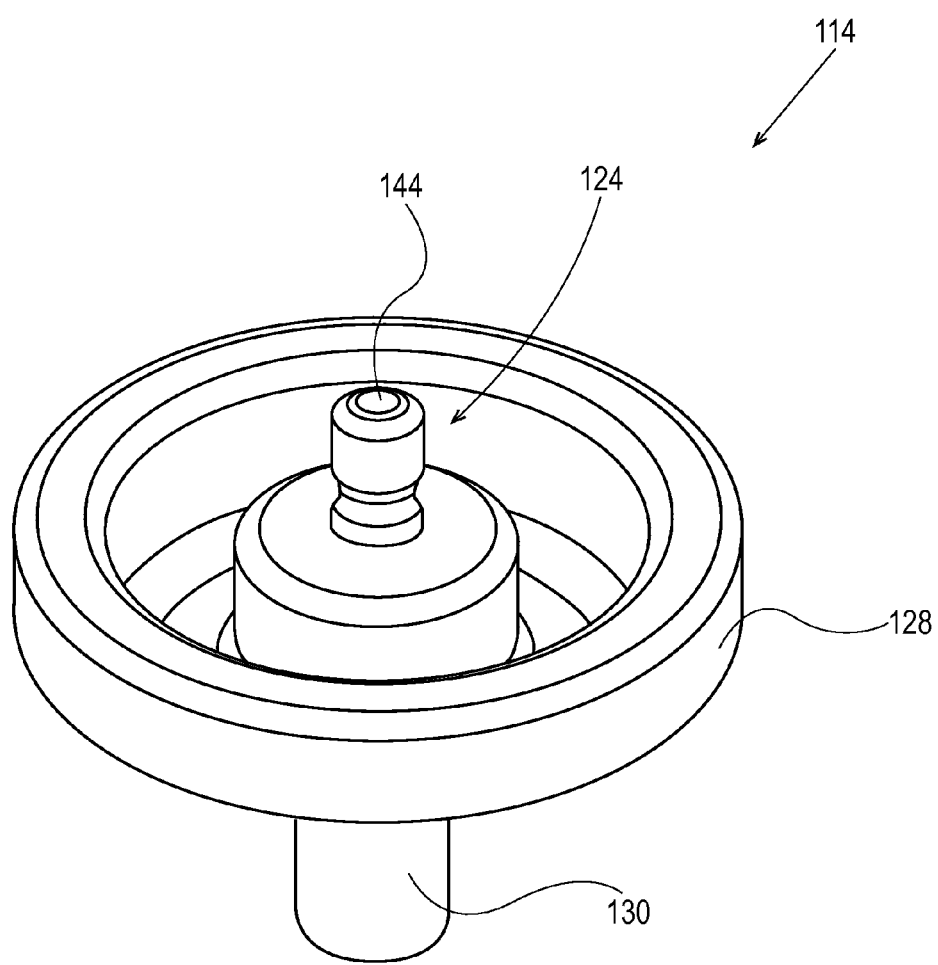
FIG. 2 is a cross-sectional view of one embodiment of a valve assembly suitable for use with the antiperspirant product of FIG. 1.
Figure 3:
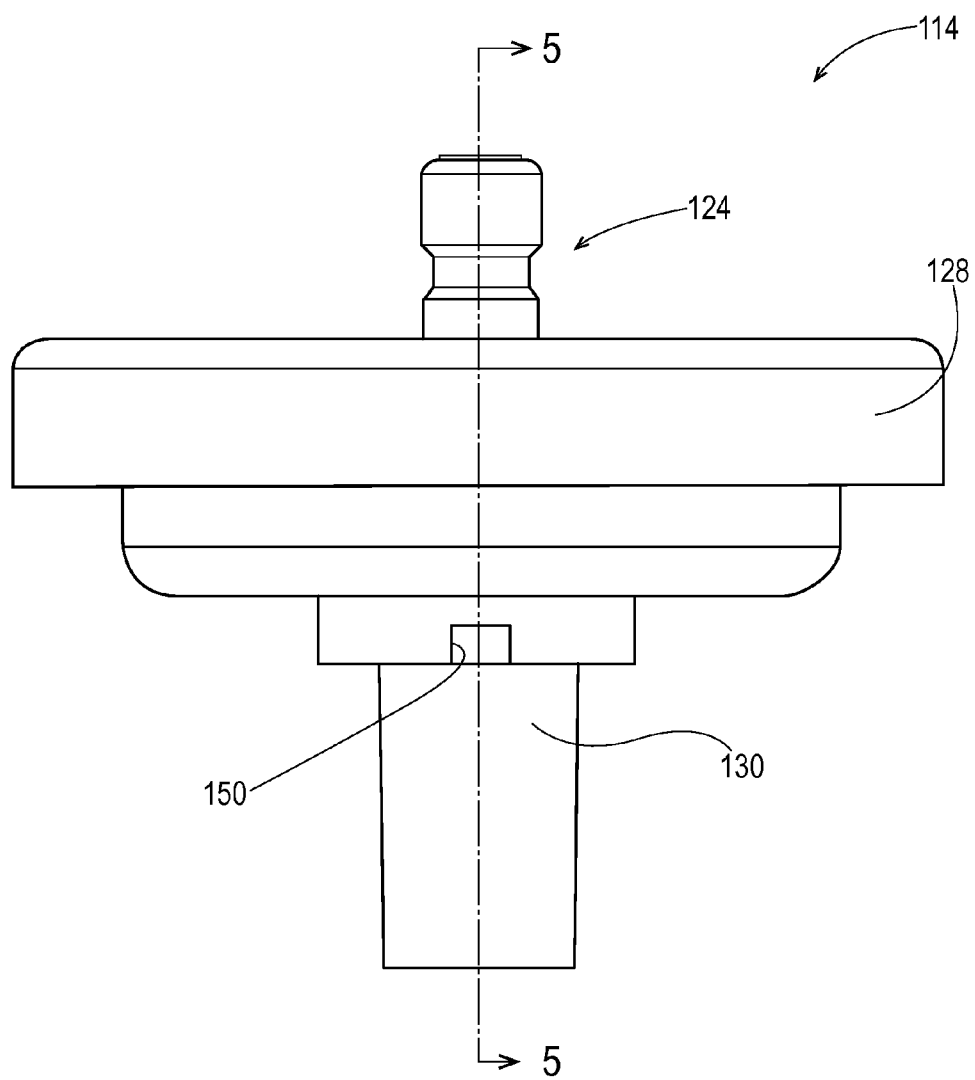
FIG. 3 is a perspective view of the stem shown in FIG. 2.

The aerosol antiperspirant compositions and propellants described herein may be incorporated into a container or package. Referring to FIGS. 1 and 2, one example of an aerosol antiperspirant product is shown. The aerosol antiperspirant product 100 comprises a container 102, a liquid propellant 104, and an aerosol antiperspirant composition 106. The container 100 comprises a body 108, an actuator 110 having a discharge orifice 112, a valve assembly 114, a dip tube 119, and a reservoir 118 that stores the liquid propellant 104 and the antiperspirant composition 106. While one reservoir is shown, a plurality of reservoirs may be provided. The actuator 110, valve assembly 114, and container 100 may be provided in a wide variety of configurations, shapes, and sizes. The volume of the reservoir 118 may be from about 20 ml to about 120 ml, or from about 40 ml to about 110 ml, or from about 70 ml to about 110 ml. An aerosol antiperspirant product may contain from about 10 g to about 60 g, or from about 15 g to about 50 g, or from about 25 g to about 50 g of total materials stored in the reservoir 118.

When a user depresses the actuator 110, a valve within the valve assembly 114 is opened thereby reducing the pressure in the reservoir 118. As the pressure drops, the liquid propellant 104 begins to boil thereby maintaining/increasing the pressure in the reservoir 118 which forces some of the antiperspirant composition 106 and liquid propellant 104 up the dip tube 119, thru the valve, and out of the discharge orifice 112 of the actuator 110. The liquid propellant mixed with the antiperspirant composition expands into a gas (within the actuator, upon exiting the actuator, or both) which atomizes the antiperspirant composition into droplets and forms a spray comprising the droplets and the gaseous propellant.

Referring to FIGS. 2 to 11, one example of a valve assembly 114 which may be attached to the body 108 is shown. The valve assembly 114 comprises a stem 124 to which the actuator 110 attaches, a mounting flange 128 for attaching the valve assembly 114 to the body 108, and a housing 130 attached to the mounting flange 128. The housing 130 contains a spring 132 that biases the stem 124. The bottom portion of the housing 130 comprises a counter bore for receiving the dip tube 119. In this particular embodiment, a valve comprises mating sealing surfaces 140 and 146 formed by an inner wall of a substantially flat gasket 148 and a wall of a groove 140 formed in the stem 124. The sealing surfaces 140 and 146 are mated when the actuator 110 is not depressed, as shown in FIG. 1, thereby preventing flow of the antiperspirant composition and liquid propellant to the actuator 110. As used herein, the term valve (as opposed to valve assembly) is intended to merely refer to the mating sealing surfaces that permit or prevent flow of the liquid antiperspirant composition (possibly mixed with propellant in a gaseous and/or liquid state) from the reservoir 118 to the actuator 110. In some specific embodiments, the valve is a continuous flow valve, meaning there is flow through the valve for as long as the actuator is depressed. In contrast, a non-continuous or metered valve allows only predetermined amount of flow thru the valve regardless how long the actuator is depressed.

One or more radial bores 138 opening into the wall of the groove 140 communicate with a blind axial bore 144 that extends along a portion of the length of the stem 124. The one or more radial bores 138 may function as a controlling orifice that principally controls the mass flow of the liquid propellant/antiperspirant composition mixture. The axial bore 144 communicates with the actuator 110 when it is attached to the stem 124. When the actuator 110 is depressed, the sealing surfaces 140 and 146 separate, thereby permitting a mixture of liquid propellant and antiperspirant composition to flow through the radial bore 138 to the axial bore 144 and onto the actuator 110. As will be appreciated, other valve configurations, sizes, and shapes may be provided, as known in the art. For example, the various valve configurations illustrated in U.S. Pat. No. 4,396,152 may also be utilized.

The controlling orifice may comprise one or a plurality of openings. The controlling orifice may have a total cross-sectional area from about 0.01 mm² to about 1 mm², or about 0.03 mm² to about 0.5 mm², or about 0.06 mm² to about 0.1 mm². The controlling orifice may have a maximum dimension, typically a diametrical dimension, from about 0.1 mm to about 1 mm, or from about 0.2 mm to about 0.8 mm, or from about 0.3 mm to about 0.5 mm. In one embodiment, the controlling orifice comprises one radial bore 138 having a diameter from about 0.3 mm to about 0.4 mm.

The valve assembly 114 may comprise a vapor tap for diverting some of the gaseous propellant from the headspace of the reservoir 118 for the purpose of mixing the diverted gaseous propellant with the antiperspirant composition. The housing 130 may comprise a one or more holes 150 for permitting gaseous propellant to pass from the reservoir 118 into the interior of the housing 130. A cup-shaped insert 152 may be installed within the housing 130. The cup-shaped insert 152 may receive one end of the spring 132, as best seen in FIG. 1. A bore 154 may be provided in the bottom of the cup-shaped insert 152, thereby permitting the antiperspirant composition/liquid propellant mixture to flow from the dip tube 119 into the interior of the cup-shaped insert 152. One or more passages 158 may be provided to direct the gaseous propellant from the interior of the housing 130 into the bore 154, where it mixes with the antiperspirant composition/liquid propellant mixture. The passages 158 may be aligned tangentially with the bore 154, as shown by way of example in FIG. 11, or the passages 158 may be aligned radially with the bore 154. The passages 158 may also be aligned in other configurations with the bore 154, such as intermediate between a tangential arrangement and a radial arrangement. If a vapor tap arrangement is provided, the passage(s) 158 may have a total cross-sectional area from about 0.05 mm² to about 0.4 mm².

While the passages are shown as generally rectangular in cross-sectional shape, it will be appreciated that the passages 158 may be provided in other shapes and sizes. Similarly, while the various bores, holes, and orifices are shown and described herein as generally circular/cylindrical in shape, it will be appreciated that they may be provided in other shapes and sizes. Further, while the vapor tap arrangements shown in the FIGS. permit gaseous propellant to mix with the antiperspirant composition/liquid propellant mixture upstream of the valve, other vapor tap arrangements (or no vapor tap) may be implemented as known in the art. For example, a vapor tap arrangement may be provided where the gaseous propellant mixes downstream of the valve, perhaps still within the valve assembly or within the actuator. Multiple vapor tap arrangements may also be provided. For example, a first vapor tap arrangement might provide for mixing of gaseous propellant and the antiperspirant composition/liquid propellant mixture upstream of the valve while a second vapor tap arrangement might provide for mixing of additional gaseous propellant and the antiperspirant composition mixture downstream of the valve. While the valve assembly is shown herein as comprising a variety of components, it is contemplated that these components may be changed, combined, deleted, or other components or structures substituted therefor without departing from the spirit and/or scope of the various invention(s) described herein. Likewise, the container and actuator may be provided in a variety of alternate shapes and configurations.

Figure 4:
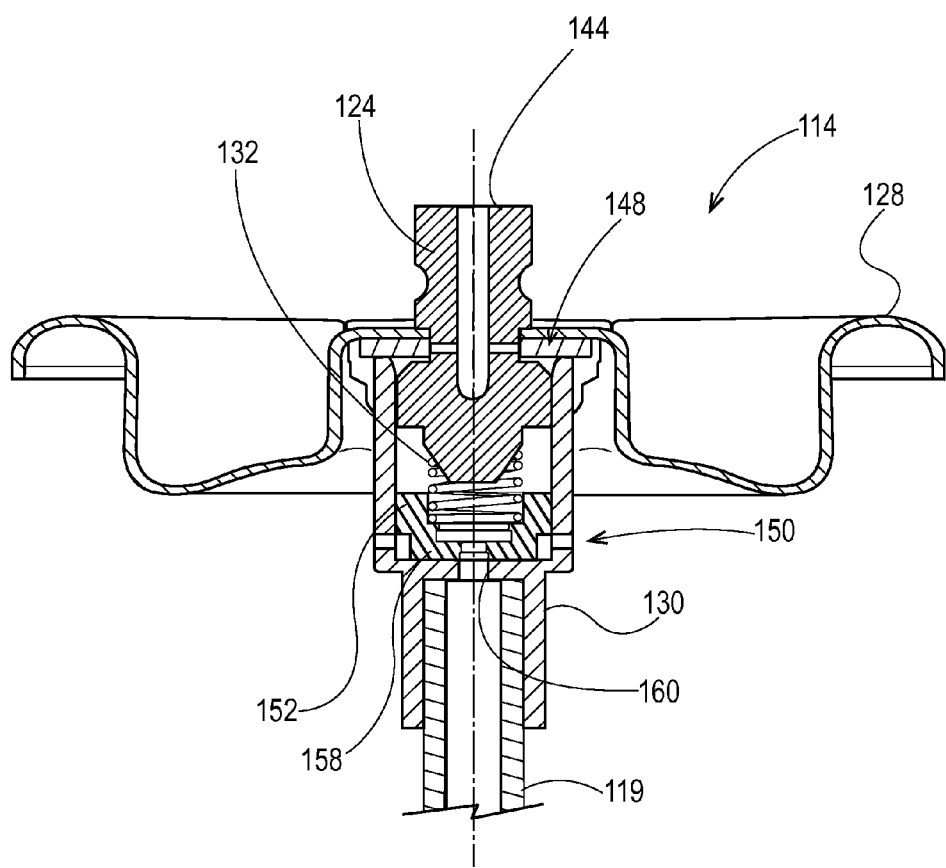
FIG. 4 is a cross-sectional view of the stem of FIG. 3, taken along line 3-3 thereof.
Figure 5:
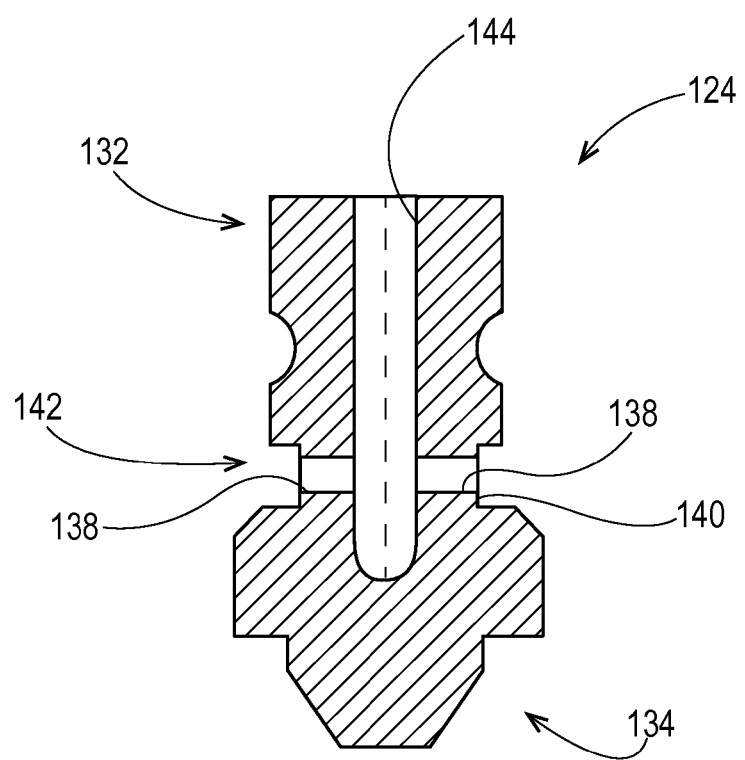
FIG. 5 is a perspective view of the housing shown in FIG. 2.
Figure 6:
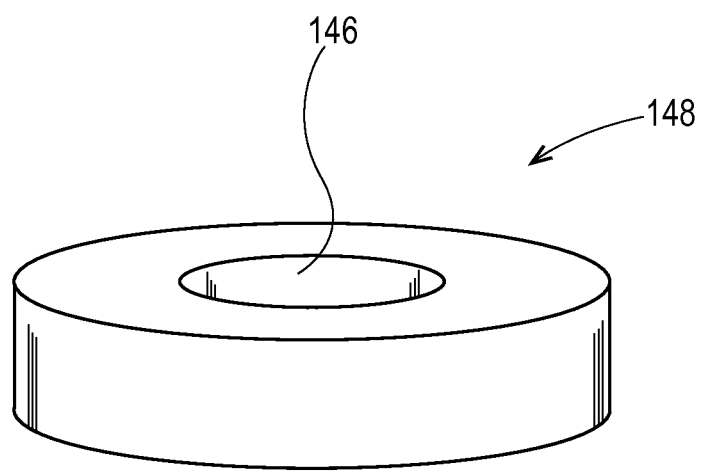
FIG. 6 is a cross-sectional view of the housing of FIG. 5, taken along line 5-5 thereof.
Figure 7:
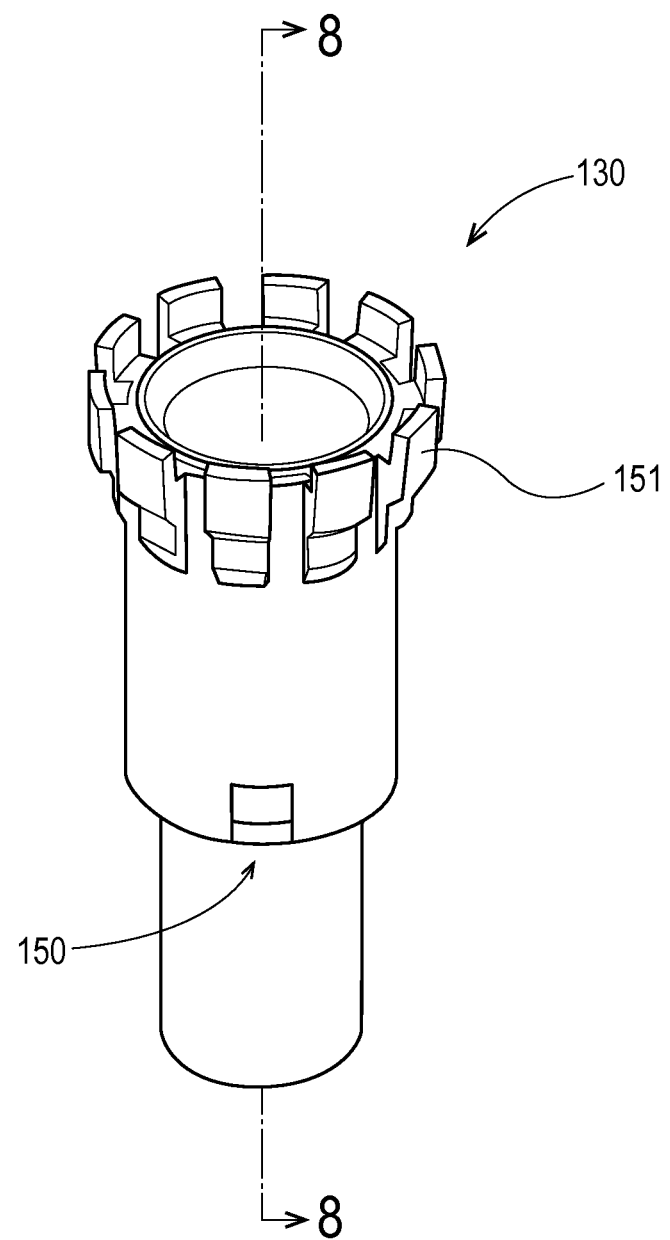
FIG. 7 is a perspective view of the gasket shown in FIG. 2.
Figure 8:
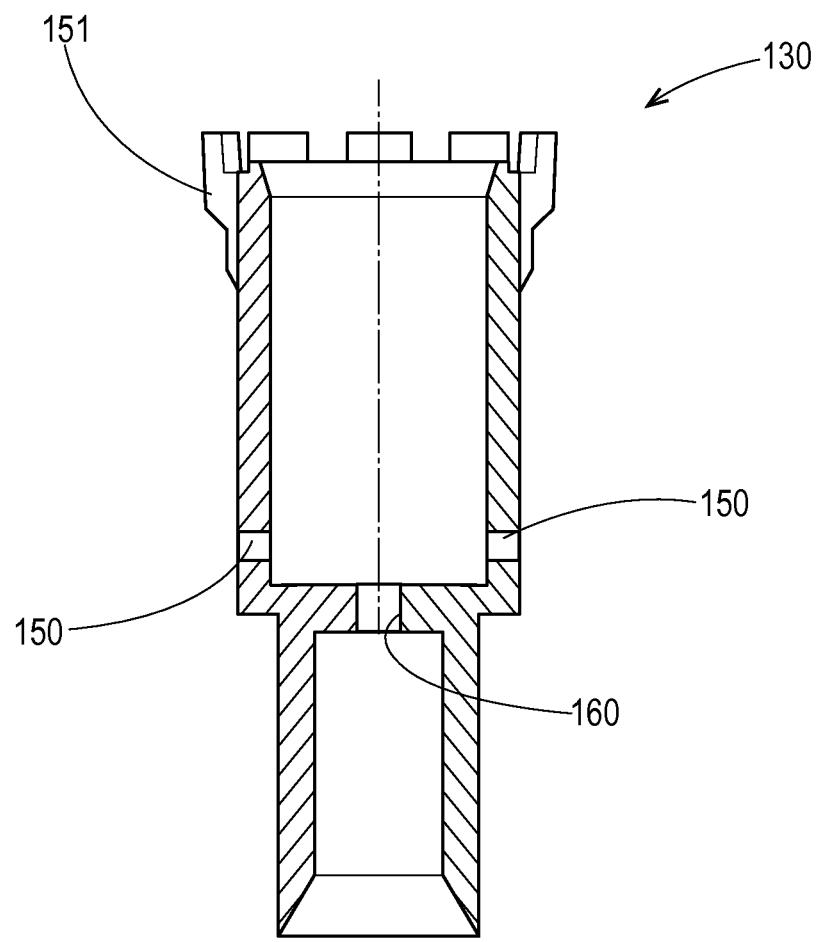
FIG. 8 is a perspective view of the cup-shaped insert shown in FIG. 2.
Figure 9:
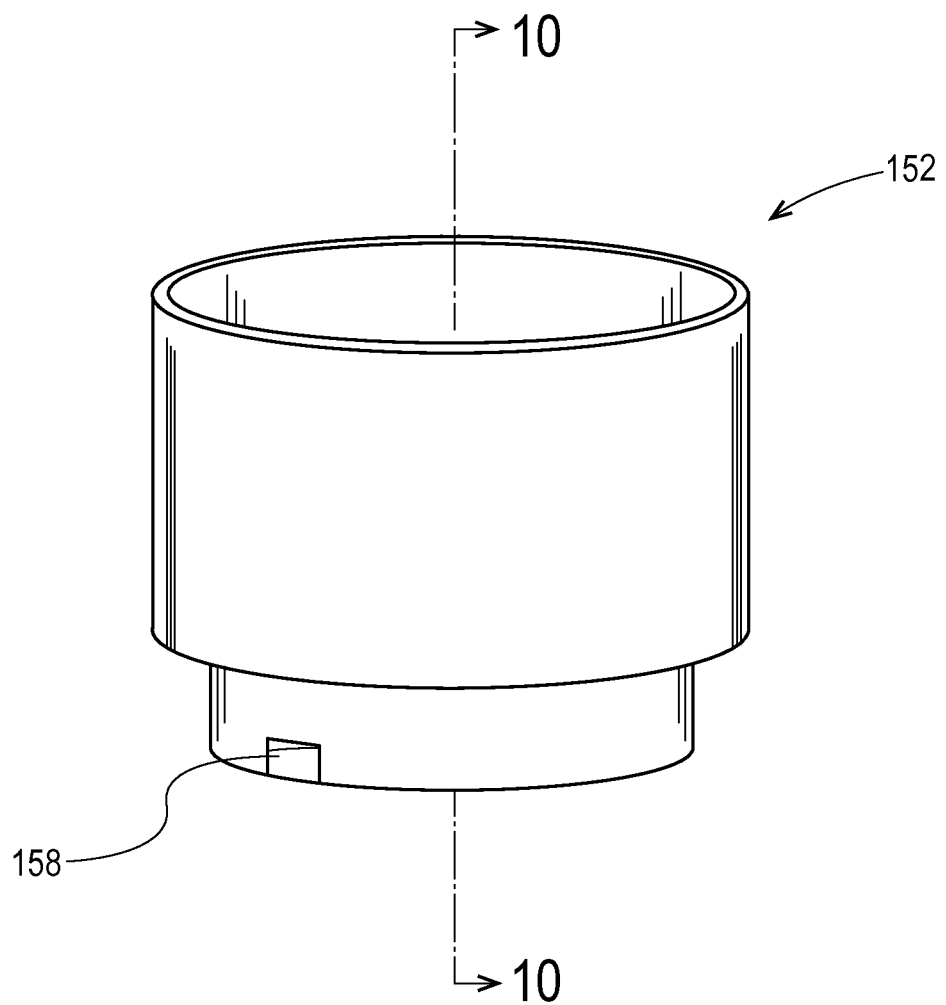
FIG. 9 is a cross-sectional view of the cup-shaped insert shown in FIG. 8, taken along line 8-8 thereof.
Figure 10:
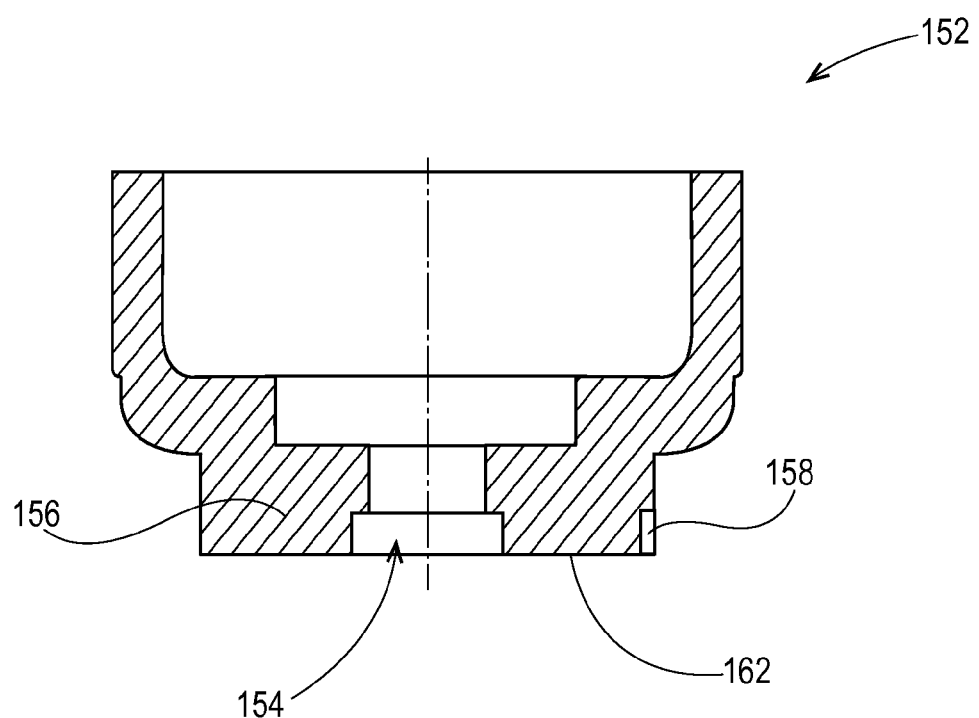
FIG. 10 is a bottom view of the cup-shaped insert shown in FIG. 8.
Figure 11:
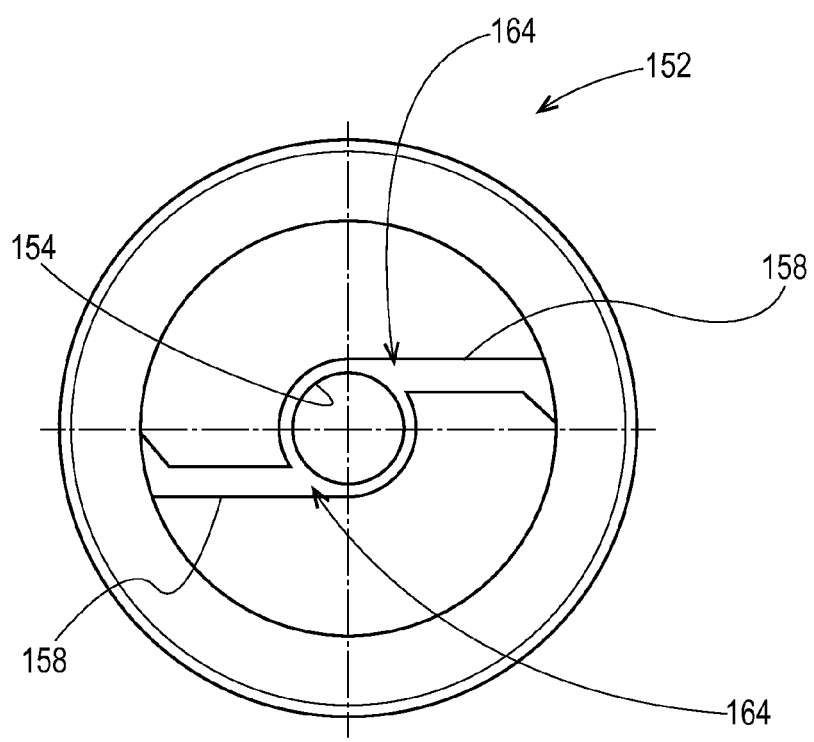
FIG. 11 is a bottom view of an alternate embodiment of the cup-shaped insert shown in FIG. 8.

One example of a valve assembly having the general configuration shown in FIG. 4 is available from the Precision Valve Company (USA) under the trade name Ecosol.

IV. Methods of Use

A user of an aerosol antiperspirant product may initiate a spray by depressing an actuator, thereby opening a valve in the product which enables a liquid propellant/antiperspirant composition mixture to exit the actuator. Prior to actuation, it may be desirable to shake or rotate the product to redisperse the liquid and particulate materials. While usage time can vary widely, users of an aerosol antiperspirant product may depress the actuator from about 2 seconds to about 5 seconds, or from about 2 seconds to about 4 seconds, or from about 2 seconds to about 3 seconds to provide a burst of antiperspirant composition for deposition to an underarm or axillia skin surface. An aerosol antiperspirant product may be sized to provide a life cycle from about 60 seconds to about 200 seconds, or from about 70 seconds to about 150 seconds, for from about 90 seconds to about 130 seconds. Aerosol antiperspirant product life cycles within these ranges may provide from about 15 to about 50 two second uses per product.

Wetness protection/product efficacy may increase as the amount of antiperspirant active delivered to skin increases, assuming the increased amount of active is available for activity (e.g., does not flake off). An aerosol antiperspirant product may deliver a total mass flow rate less than 0.5 g/sec or from about 0.1 g/sec to about 0.5 g/sec, or from about 0.2 g/sec to about 0.4 g/sec, or from about 0.25 g/sec to about 0.35 g/sec. An aerosol antiperspirant product may deliver an antiperspirant composition mass flow rate less than 0.3 g/sec or from about 0.1 g/sec to about 0.3 g/sec. It is believed that mass flow rates greater than described above may lead to significantly reduced skin feel (even if the L/P ratio is within the ranges previously described), because the total amount of antiperspirant composition deposited on the skin, particularly where there is a high concentration of a non-volatile silicone fluid, may be too great.

The amount of antiperspirant active delivered to a target surface (according to the test method described herein) by a two second application from an aerosol antiperspirant product may be from about 40 mg, 50 mg, 60 mg, or 70 mg to about 100 mg, 90 mg, or 80 mg. The amount of free fragrance material delivered to a target surface by a two second application of an aerosol antiperspirant product may be from about 3 mg to about 20 mg, or from about 6 mg to about 15 mg, or from about 6 mg to about 12 mg. The amount of encapsulated fragrance material delivered to a target surface by a two second application of an aerosol antiperspirant product may be from about 0.75 mg to about 15 mg, or from about 1 mg to about 12 mg, or from about 1 mg to about 9 mg. The total amount of antiperspirant composition delivered to a target surface (according to the test method described herein) by a two second application of an aerosol antiperspirant product may be from about 0.1 g to about 0.4 g, or from about 0.2 g to about 0.4 g, or from about 0.2 g to about 0.3 g.

An aerosol antiperspirant product utilizing a low propellant concentration may provide a deposition efficiency from about 60%, 65%, 70%, or 75% to about 100%, 95%, 90%, 85% or 80% for the antiperspirant composition, antiperspirant active, free fragrance materials and/or encapsulated fragrance materials.

The values described in this section may be measured according the test methods described herein.

V. Test Methods

The following test methods may be used to measure various characteristics of an antiperspirant composition, antiperspirant product, and their methods of use.

Propellant Concentration Test Method

One method for determining liquid propellant concentrations of an aerosol antiperspirant product will now be described. The overcap of the product container is removed, and the weight of the container and its contents (gross mass) are measured using any suitable scale, such as an analytical balance. The top of the container is punctured using any suitable tool, such as an AC-PD Aerosol Can Puncturing Device available from Aero-Tech Laboratory Equipment Company, LLC of Missouri, USA. The puncture needle is fully extended into the container, and the puncture needle is slowly retracted to permit the gaseous propellant to evacuate the container. Once the puncture needle is completely retracted from the container, the puncturing device can be removed from the container, and the propellant will continue to escape from the puncture in the container. All the propellant is allowed to evacuate from the container.

The mass of the container and the remaining contents (less the propellant) are measured using any suitable device, such as an analytical balance. The actuator is removed from the container using any suitable device, such as an Aero-Tech Can Decrimper available from Aero-Tech Laboratory Equipment Company, LLC of Missouri, USA. The inside of the container is rinsed with ethanol until visually clean and the container is allowed to dry for at least 2 hours. The mass of the empty container and actuator are measured using any suitable device, such as an analytical balance. The propellant mass and concentration may be determined using the following equations:

$$\text{Propellant Mass (g)} = \text{Gross Mass} - \text{Mass after Propellant Evacuation}$$

$$\text{Propellant Concentration \%} = \frac{\text{Propellant Mass}}{\text{Gross Mass} - \text{Mass of Empty Container}}$$

Total Mass Flow Rate Test Method

One method for measuring the total mass flow rate of an aerosol antiperspirant product will now be described. This test method is preferably utilized with aerosol antiperspirant products comprising a continuous actuator, meaning actuating the actuator results in a continuous rather than intermittent spray. At least four aerosol antiperspirant product samples are tested. The product samples are shaken as directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. The product samples are then removed from the bath and excess moisture is removed by blotting with a paper towel. The products samples are shaken if directed and the actuator is actuated for 5 seconds, which may be accurately timed by use of a stopwatch. Each product sample is again weighed, after which the product samples are returned to the constant-temperature bath. The process of bathing, actuating, and weighing is repeated three times for each product sample. The average total mass flow rate may be calculated from the spray time period (5.0 seconds) and the difference in mass before and after each five second spray, averaged across the four product samples and three repetitions per product sample.

Antiperspirant Composition Mass Flow Rate Test Method

One method for measuring the antiperspirant composition mass flow rate of an aerosol antiperspirant product will now be described. This test method is preferably utilized with aerosol antiperspirant products comprising a continuous actuator, meaning actuating the actuator results in a continuous rather than intermittent spray. At least four aerosol antiperspirant product samples are tested. The product samples are shaken if directed and then immersed in a constant-temperature (25 C) bath until the internal pressure stabilizes at a temperature of 25° C. The product samples are then removed from the bath and excess moisture is removed by blotting with a paper towel. Each product sample is weighed to measure its mass using any suitable device, such as an analytical balance. Twelve large plastic bags (one for each product sample times three repetitions) having a suitable volume, such as a 1 L Ziploc brand bag (or a Whirl-Pak Write-on 55 ounce bag, Part # B01195WA available from Nasco, Inc), are weighed to measure their mass using any suitable device, such as an analytical balance. Each product sample is shaken if directed and sprayed into one of the bags for a period of 5 seconds in a manner that minimizes antiperspirant composition from exiting the bag. For example, the opening thru which the spray enters the bag may be limited to about 5 cm. The 5 second spray time period may be accurately measured using a stopwatch. Following the 5 second spray period, the antiperspirant composition is allowed to settle within the bag and the bag remains open for at least 1 minute but not longer than 2 minutes in order to allow the liquid propellant to evaporate. The weight of the bags and their contents are weighed to measure their mass, and the product samples are also weighed. The average mass flow rate of the antiperspirant composition may be determined using the following equation which is averaged across the four product samples and the three repetitions per product sample:

Mass Flow Rate of Antiperspirant Composition(g/sec)=Weight of Bag and Antiperspirant Composition−Weight of Bag/5 seconds Antiperspirant Composition Deposition Efficiency, Amount Dispensed, and Amount Deposited Test Methods One method for measuring antiperspirant composition deposition efficiency, amount dispensed and amount deposited of an aerosol antiperspirant product will now be described. At least four aerosol antiperspirant product samples are tested. The product samples are shaken if directed and the actuator is actuated for 2 to 3 seconds, after which each product sample is weighed to measure its mass using any suitable device, such as an analytical balance. The product samples are then immersed in a constant-temperature (25 C) bath until the internal pressure stabilizes at a temperature of 25° C. At least twelve filter papers, such as Whatman 150 mm (diameter) Filter Paper available under the catalog number 1003-150 from the Whatman Company of the UK, are weighed to measure the mass of the filter using any suitable device, such as an analytical balance. The product samples are removed from the bath, and any excess moisture is removed by blotting with a paper towel. The product samples are shaken if directed, and the product sample is positioned approximately 15 cm away from one of the filter papers, which is preferably weighted and/or fixtured to assure the filter paper does not move during spraying. The actuator of the product sample is actuated for 5 seconds which may be accurately timed using a stopwatch. It will be appreciated, however, that other spray times may be substituted. For example, a two second spray time period might be used to better approximate the amount dispensed/deposited during a typical use cycle by a consumer. The spray from the product sample should be centered on the center of the filter paper. After spraying, the filter paper and product sample are weighed to measure the mass using any suitable device, such as an analytical balance. The steps of bathing, weighing, and actuating are repeated three times for each of the product samples. The average antiperspirant composition efficiency may be calculated using the following equations, averaged across the four product samples and the three repetitions per product sample:

Amount Dispensed (g) = Product Sample Weight Before Spraying −

Product Sample Weight After Spraying

Amount Deposited (g) = Filter Paper Weight After Spraying −

Filter Paper Weight before Spraying

Antiperspirant Composition Deposition Efficiency (%) =

$$100 \times \frac{\text{Amount Deposited}}{\text{Amount Dispensed} * \textit{Antiperpsirant Composition Weight \%}}$$

Antiperspirant Active Deposition Efficiency, Amount Dispensed, and Amount Deposited Test Methods One method for measuring the antiperspirant active deposition efficiency of an aerosol antiperspirant product will now be described. At least four aerosol antiperspirant product samples are tested. The product samples are shaken if directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. The product samples are then removed from the bath and excess moisture is removed by blotting with a paper towel. At least twelve filter papers, such as Whatman 150 mm Filter Paper available under the catalog number 1003-150 from the Whatman Company of the UK, are weighed to measure the mass of the filter using any suitable devices, such as an analytical balance. The product samples are removed from the bath, and any excess moisture is removed by blotting with a paper towel. The product samples are shaken if directed, and the product sample is positioned approximately 15 cm away from one of the filter papers, which is preferably weighted and/or fixtured to assure the filter paper does not move during spraying. The actuator of the product sample is actuated for 5 seconds which may be accurately timed using a stopwatch. It will be appreciated that other spray times may be substituted. For example, a two second spray time period might be used to better approximate the amount dispensed/deposited during a typical use cycle by a consumer. The spray from the product sample should be centered on the center of the filter paper. After spraying, the filter paper and product sample are weighed to measure the mass using any suitable device, such as an analytical balance. The steps of bathing, weighing, and actuating are repeated three times for each of the product samples. The amount of antiperspirant active deposited on a filter paper may be determined using an automated titrator, such as MettlerDL-70 equipped with Mettler DM141C combination silver-silver chloride electrode available from Mettler, Inc. Alternatively, the amount of antiperspirant active deposited on a filter paper may be determined using the Content of Chloride Method set forth in the USP monograph for aluminum chlorohydrate (USP 35) or an equivalent method. The average antiperspirant active deposition efficiency may be calculated using the following equations, averaged across the four product samples and the three repetitions per product sample:

Amount Dispensed (g) = Product Sample Weight Before Spraying −

Product Sample Weight After Spraying

Amount Deposited (gm) = Filter Paper Weight Before Spraying −

Filter Paper Weight After Spraying

Antiperspirant Composition Efficiency (%) =

$$100 \times \frac{\text{Amount Deposited}}{\text{Amount Dispensed} * \textit{Antiperpsirant Composition Weight \%}}$$

VI. Examples

Examples 1, 2 and 3 further describe and demonstrate some non-limiting embodiments of antiperspirant compositions made in accordance with the invention, while Example 4 is a comparative antiperspirant composition. The examples are given solely for the purpose of illustration and are not to be construed as limitations of the invention as many variations thereof are possible without departing from the spirit and the scope of the invention.

TABLE 1

| Ingredient | Example 1 | Example 2 | Example 3 | Comparative Example 4 |
|---|---|---|---|---|
| Aluminum chlorohydrate[1] | 28 | 28 | 19 | 28 |
| Dimethicone | 48.38 | 52.3 | 61.25 | 5 |
| Cyclopentasiloxane[2] | | | | 47.25 |
| Hydrophobic tapicoa[3] | 12 | | | |
| Hydrophilic tapioca[4] | | 12 | 12 | 12 |
| Disodium Hectorite[5] | 2 | | | |
| Triethyl citrate | 0.67 | | | |
| Silicone gum[6] | 1 | | | |
| Hydrophilic silica[7] | | 1 | 1 | 1 |
| Hydrophobic silica[8] | | 0.25 | 0.25 | 0.25 |
| Perfume | 3.5 | 3.5 | 3.5 | 3.5 |
| Betacyclodextrin fragrance | 3 | 3 | 3 | 3 |

The values are shown on a by weight of the antiperspirant composition basis.
[1] 86% assay of anhydrous active, average particle size approximately 15 microns.
[2] DC 200 Fluid (50 cst) available from Dow Corning
[3] Dry Flo TS from Akzo Nobel
[4] Tapioca Pure from Akzo Nobel
[5] Bentone 38 available from Elementis
[6] DC1503 (a mixture of dimethicone and dimethiconol) available from Dow Corning
[7] Aerosil A300 silica from Evonik
[8] Aerosil A300 silica from Evonik Antiperspirant compositions of Table 1 were made using the following general batch method: the non-volatile silicone fluid (and volatile silicone fluid in the case of comparative Example 4) was added to an appropriately sized container followed by the silica (or clay in the case of Example 1) and the mixture was milled for at least 1 minute at a speed of 10,000 to 12,000 rpm using a hand held mill. In the case of Example 1, triethyl citrate was then added to the mixture and milled for at least 5 minutes. The antiperspirant active particles were added to the mixture and milled for at least 1 minute (Examples 2, 3 and 4) or at least 5 minutes (Example 1). The tapioca starch material and beta-cyclodextrin fragrance were added to the mixture and milled for at least one minute (Examples 2, 3 and 4) or at least 5 minutes (Example 1). The perfume was then added (and in the case of Example 1, the silicone gum) and milled for at least one minute.

Antiperspirant compositions of Example 1 had an average viscosity of approximately 1,500 centipose, and antiperspirant compositions of Example 2 had an average viscosity of approximately 4,200 centipose. Antiperspirant compositions of Example 3 had an average viscosity of approximately 3,000 centipose. Antiperspirant compositions of comparative Example 4 had an average viscosity of approximately 1,400 centipose. The viscosity measurements were made using a Brookfield Viscometer Model 1/2RVT using an RV-4 spindle using techniques well known in the art. The desired weight (approximately 15 g) of the antiperspirant composition was transferred to 55 ml product containers to which a valve assembly was affixed. Approximately 15 g of A-46 propellant was added to the product containers to achieve a 50% propellant concentration and 50% antiperspirant composition concentration by weight of the total fill of materials.

The average pressure within the reservoir was approximately 375 kPa for aerosol products containing the antiperspirant composition of Example 1, and approximately 393 kPA for aerosol products containing the antiperspirant composition of Example 2. The average pressure within the reservoir was approximately 365 kPA for aerosol products containing the antiperspirant composition of Example 3. The average pressure within the reservoir was approximately 379 kPA for aerosol products containing the antiperspirant composition of comparative Example 4. Pressure within the reservoir was measured using a pressure gauge and techniques well known in the art. The valve assembly was similar to that shown in FIGS. 1 to 10, having one radial bore 160 with a diameter of approximately 0.33 mm and two passages 180 each having a width of approximately 0.25 mm and a height of approximately 0.33 mm. An actuator having a discharge orifice 112 with a diametrical dimension of approximately 0.33 mm was fitted on the valve assembly.

Aerosol products comprising the antiperspirant composition of Example 1 had an average total mass flow rate of approximately 0.37 g/sec and an average antiperspirant composition flow rate of approximately 0.17 g/sec. Aerosol products comprising the antiperspirant composition of Example 2 had an average total mass flow rate of approximately 0.38 g/sec and an average antiperspirant composition flow rate of approximately 0.18 g/sec. Aerosol products comprising the antiperspirant composition of Example 3 had an average total mass flow rate of approximately 0.36 g/sec and an average antiperspirant composition flow rate of approximately 0.17 g/sec. Aerosol products comprising the antiperspirant composition of comparative Example 4 had an average total mass flow rate of approximately 0.39 g/sec and an average antiperspirant composition flow rate of approximately 0.18 g/sec.

An en vivo study was conducted using aerosol products comprising the antiperspirant compositions of Examples 1, 2 and 3 and a commercially available aerosol antiperspirant product. The ingredient listing for the commercially available product was as follows: butane, isobutene, propane, cyclomethicone, aluminum chlorohydrate, parfum, disteardimonium hectorite, dimethiconol, PVM/MA copolymer, sodium starch octenylsuccinate, mannitol, alpha-isomethyl ionone, butylphenyl methylpropionyl, citronellol, eugenol, geraniol, hexyl cinnamyl, 1-limonene and linalool. The commercially available aerosol antiperspirant product had an average propellant concentration of approximately 85% and an average reservoir pressure of approximately 410 kPA. The commercially available antiperspirant product also had an average total mass flow rate of approximately 1.02 g/sec, and an average antiperspirant composition mass flow rate of approximately 0.20 g/sec.

Forty-eight subjects were enrolled in the study, of which 45 completed the study. The study lasted 26 days, comprising a 21 day washout period in which the subjects used no antiperspirant products (deodorant products only were applied) followed by a 5 day treatment period with the aerosol antiperspirant products. The antiperspirant products were applied once each morning, for 2 seconds from a 6 inch distance by the clinical site personnel, during the 5 day treatment period. Hot room evaluations for sweat production were conducted prior to start of the 5 day treatment period (baseline) and 12 hours post the $5^{th}$ day of the treatment period. The adjusted mean sweat values (mg sweat) at the start of the study (baseline) and twelve hours post treatment day 5 are shown in Table 2 below.

TABLE 2

|  | Mean Sweat at Baseline (mg of sweat collected) | Baseline Adjusted Mean Sweat Value 12 hrs Post Treatment Day #5 (mg of sweat collected) |
| --- | --- | --- |
| Aerosol Products with Antiperspirant Composition of Example 1 | 595 | 382 |
| Aerosol Products with Antiperspirant Composition of Example 2 | 591 | 362 |
| Aerosol Products with Antiperspirant Composition of Example 3 | 665 | 343 |
| Aerosol Products with Antiperspirant Composition of Comparative Example 4 | 676 | 405 |
| Commercially Available Aerosol Product | 591 | 439 |

After five days of treatment, the aerosol antiperspirant products comprising the antiperspirant compositions of Examples 1, 2 and 3 resulted in lower mean sweat values (mg of sweat) twelve hours post treatment day #5 than both the commercially available antiperspirant product and comparative Example 4. A lower mean sweat value means less perspiration was released from the eccrine glands in the underarm area to the skin surface, and therefore the antiperspirant product had a higher product efficacy. The results for the aerosol products of Examples 2 and 3 were statistically significant (with at least a 90% confidence level). The results for the composition of Example 3 are particularly notable, as this composition had the lowest concentration of antiperspirant active among Examples 1, 2, and 3 and yet had the lowest mean sweat value post treatment among the tested antiperspirant compositions. This may be due to the higher dimethicone concentration, which may have increased substantivity of the antiperspirant active on skin compared to the antiperspirant compositions of Examples 1 and 2. The commercially available product, which had the highest propellant concentration, had the highest mean sweat value post treatment despite having the highest antiperspirant mass flow rate among the products. This may be due, at least in part, to the low antiperspirant composition deposition efficiency of the commercially available product in combination with a lack of antiperspirant active substantivity resulting from the use of a volatile silicone fluid as the liquid carrier. The mean sweat value post treatment for the antiperspirant compositions of Example 2 were directionally better than the value for the compositions of Example 3, possibly due to the hydrophilic tapioca material enabling better antiperspirant active release compared to the hydrophobically modified tapioca material of Example 3. The mean sweat value post treatment for antiperspirant compositions of comparative Example 4 was directionally worse than the value for the antiperspirant compositions of Example 2. This may be due to reduced antiperspirant active substantivity resulting from use of the volatile silicone fluid in comparative Example 4 compared to use of a non-volatile silicone fluid in the antiperspirant compositions of Example 2.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, including without limitation U.S. Ser. No. 61/701,201 filed Sep. 14, 2012, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aerosol antiperspirant composition, comprising:
   a propellant;
   an antiperspirant composition comprising:
      one or more liquid materials comprising 70% to 100% by weight of the liquid materials, of non-volatile polydimethyl siloxane fluid; the one or more liquid materials having a concentration from 40% to 70% by weight of the antiperspirant composition;
      antiperspirant active particulates having a concentration from about 16% to about 32% by weight of the antiperspirant composition;
      one or more non-antiperspirant active particulates that are substantially inert, wherein the one or more non-antiperspirant active particulates that are substantially inert have a concentration from 10% to 30% by weight of the antiperspirant composition; and
      wherein the antiperspirant composition has a total particulate concentration from 30% to about 60% by weight of the antiperspirant composition.

2. An aerosol antiperspirant composition according to claim 1, wherein the one or more liquid materials of the antiperspirant composition consist essentially of the non-volatile polydimethyl siloxane fluid, a liquid fragrance material and a silicone gum.

3. An aerosol antiperspirant composition according to claim 1, wherein the non-volatile silicone fluids have a concentration from about 40% to 55% by weight of the antiperspirant composition.

4. An aerosol antiperspirant composition according to claim 1, wherein the total particulate concentration is from 40% to about 50% by weight of the antiperspirant composition.

5. An aerosol antiperspirant composition according to claim 1, wherein the antiperspirant composition is substantially or completely free of a silicone gum.

6. An antiperspirant composition according to claim 1, wherein the non-volatile silicone fluid has a viscosity from 5 centistokes to 900 centistokes.

7. An aerosol antiperspirant composition according to claim 1, wherein the ratio of total liquid materials to total particulate materials is from about 0.6 to about 1.4.

8. An aerosol antiperspirant composition according to claim 1, wherein the non-volatile silicone fluids consists essentially of a polydimethyl siloxane fluid having a viscosity of about 10 centistokes to about 350 centistokes.

9. An aerosol antiperspirant composition according to claim 1, herein the ratio of total liquid materials to total particulate materials is from about 0.6 to about 1.6.

10. An antiperspirant composition according to claim 1, wherein the one or more liquid materials comprise less than 10% by weight of volatile silicone fluids.

11. An antiperspirant composition according to claim 1, wherein the antiperspirant composition is substantially or completely free of volatile silicone fluids.

12. An aerosol antiperspirant composition according to claim 1, wherein the particulates of the antiperspirant active have a concentration less than 34% by weight of the antiperspirant composition.

13. An aerosol antiperspirant composition according to claim 1, further comprising one or more bulking or suspending materials selected from the group consisting of a silica material, a clay material and combinations thereof.

14. An aerosol antiperspirant composition according to claim 1, wherein the one or more non-antiperspirant active particulates are selected from the group consisting of particulate fragrance materials, native starches and combinations thereof.

15. An aerosol antiperspirant composition according to claim 1, wherein the antiperspirant composition has a viscosity greater than 3,000 centipoises.

16. An aerosol antiperspirant composition according to claim 1, wherein the propellant has a concentration from about 40% to 65% by weight of the aerosol antiperspirant composition.

17. A product, comprising a reservoir, an actuator comprising a discharge orifice, and a valve in fluid communication with the discharge orifice and the reservoir, the reservoir storing an aerosol antiperspirant composition according to claim 1.

* * * * *